（12) United States Patent
Annaluru et al.

(10) Patent No.: US 12,415,984 B2
(45) Date of Patent: Sep. 16, 2025

(54) **MODIFIED *AGROBACTERIUM* STRAINS AND USE THEREOF FOR PLANT TRANSFORMATION**

(71) Applicant: PIONEER HI-BRED INTERNATIONAL, INC., Johnston, IA (US)

(72) Inventors: Sai Viswanath Narayana Annaluru, Grimes, IA (US); Steven Henry Bass, Hillsborough, CA (US)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 511 days.

(21) Appl. No.: 17/440,303

(22) PCT Filed: Mar. 26, 2020

(86) PCT No.: PCT/US2020/024993
§ 371 (c)(1),
(2) Date: Sep. 17, 2021

(87) PCT Pub. No.: WO2020/198496
PCT Pub. Date: Oct. 1, 2020

(65) Prior Publication Data
US 2022/0154193 A1   May 19, 2022

Related U.S. Application Data

(60) Provisional application No. 62/825,054, filed on Mar. 28, 2019.

(51) Int. Cl.
*C12N 1/20* (2006.01)
*C12N 15/82* (2006.01)

(52) U.S. Cl.
CPC ............ *C12N 1/20* (2013.01); *C12N 15/8205* (2013.01)

(58) Field of Classification Search
CPC .............................. C12N 1/20; C12N 15/8205
See application file for complete search history.

(56) References Cited

U.S. PATENT DOCUMENTS

| 4,567,141 | A  | 1/1986  | Olsen |
| 8,334,429 | B2 | 12/2012 | Ranch et al. |
| 8,581,045 | B2 | 11/2013 | Farrand et al. |
| 9,617,551 | B2 | 4/2017  | Merlo et al. |
| 9,765,350 | B2 | 9/2017  | Gupta et al. |
| 2006/0014257 | A1 | 1/2006 | Katashkina et al. |

(Continued)

FOREIGN PATENT DOCUMENTS

| EP | 2 980 214 A1 | 2/2016 |
| WO | 2018226506 A1 | 12/2018 |
| WO | 2019027790 A1 | 2/2019 |

OTHER PUBLICATIONS

Kim, Sung-Ryul, and Gynheung An. "Bacterial transposons are co-transferred with T-DNA to rice chromosomes during Agrobacterium-mediated transformation." Molecules and cells 33 (2012): 583-589. (Year: 2012).*

(Continued)

*Primary Examiner* — Louise W Humphrey
*Assistant Examiner* — Rachel Emily Martin

(57) ABSTRACT

Modified *Agrobacterium* strains, methods of producing such modified *Agrobacterium* strains, and methods of using such modified *Agrobacterium* strains for producing transformed plants are disclosed herein.

13 Claims, 1 Drawing Sheet

Specification includes a Sequence Listing.

(56) References Cited

U.S. PATENT DOCUMENTS

| | | |
|---|---|---|
| 2010/0186122 A1 | 7/2010 | Ranch et al. |
| 2011/0126324 A1 | 5/2011 | Farrand et al. |
| 2017/0121722 A1 | 5/2017 | Anand et al. |

OTHER PUBLICATIONS

GenBank accession CP007227.1 (https://www.ncbi.nlm.nih.gov/nuccore/CP007227.1?report=genbank&to=556485) (Year: 2016).*
NCBI Blast results showing sequence identity with GenBank accession CP007227.1 deposited in 2016 (Year: 2016).*
International Preliminary Report on Patentability for International Application No. PCT/US2020/024993, mailed Oct. 7, 2021, 10 Pages.
International Search Report and Written Opinion for PCT/US2020/024993 issued Jun. 16, 2020.
Gelvin; "Improving plant genetic engineering by manipulating the host"; Trends in Biotechnology (Mar. 2003) 21(3):95-98.
Gelvin; "Agrobacterium-Mediated Plant Transformation: the Biology behind the 'Gene-Jockeying' Tool"; Microbiology and Molecular Biology Reviews (Mar. 2003) 67(1):16-37.
Gelvin; "Agrobacterium-mediated DNA transfer, and then some"; Nature Biotechnology (Sep. 2008) 26(9):998-1000.
Gupta, et al.; "ARG-ANNOT, a New Bioinformatic Tool To Discover Antibiotic Resistance Genes in Bacterial Genomes"; Antimicrobial Agents and Chemotherapy (Jan. 2014) 58(1):212-220.
Hamlett, et al.; "Roles of the Tn21 merT, merP, and merC Gene Products in Mercury Resistance and Mercury Binding"; Journal of Bacteriology (Oct. 1992) 174(20):6377-6385.
Hansen, et al.; "The Prevalence of the OqxAB Multidrug Efflux Pump amongst Olaquindox-Resistant *Escherichia coli* in Pigs"; Microbial Drug Resistance (2005) 11(4):378-383.
Hoekema, et al.; "A binary plant vector strategy based on separation of vir- and T-region of the Agrobacterium tumefaciens Ti-plasmid"; Nature (May 1983) 303(12):179-180.
Jacoby; "Properties of R Plasmids Determining Gentamicin Resistance by Acetylation in Pseudomas aeruginosa"; Antimicrobial Agents and Chemotherapy (Sep. 1974) 6(3):239-252.
Kim and An; Bacterial Transposons Are Co-Transferred with T-DNA to Rice Chromosomes during Agrobacterium-Mediated Transformation; Molecules and Cells (Jun. 30, 2012) 33:583-589.
Klapwijk, et al.; "Transposition of Tn904 Encoding Streptomycin Resistance into the Octopine Ti Plasmid of Agrobacterium tumefaciens"; Journal of Bacteriology (Jan. 1980) 141(1):129-136.
Komari, et al.; "Physical and Functional Map of Supervirulent Agrobacterium tumefaciens Tumor-Inducing Plasmid pTiBo542"; Journal of Bacteriology (Apr. 1986) 166(1):88-94.
Kumar and Doerrler; "Members of the Conserved DedA Family Are Likely Membrane Transporters adn Are Required for Drug Resistance in *Escherichia coli*"; Antimicrobial Agents and Chemotherapy (Feb. 2014) 58(2):923-930.
Nucifora, et al.; "Mercury Operon Regulation by the merR Gene of the Organomercurial Resistance System of Plasmid pDU1358"; Journal of Bacteriology (Aug. 1989) 171(8):4241-4247.
Ooms, et al.; "Octopine Ti-Plasmid Deletion Mutants of Agrobacterium tumefaciens with Emphasis on the Right Side of the T-Region"; Plasmid (1982) 7:15-29.
Ooms, et al.; "Characterization of Tn904 Insertions in Octopine Ti Plasmid Mutants of Agrobacterium tumefaciens"; Journal of Bacteriology (Oct. 1980) 144(1):82-91.
Silver and Misra; "Plasmid-Mediated Heavy Metal Resistances"; Ann. Rev. Microbiol. (1988) 42:717-743.
Sulavik, et al.; "Antibiotic Susceptibility Profiles of *Escherichia coli* Strains Lacking Multidrug Efflux Pump Genes"; Antimicrobial Agents and Chemotherapy (Apr. 2001) 45(4):1126-1136.
Tal and Schuldiner; "A coordinated network of transporters with overlapping specificities provides a robust survival strategy"; PNAS (Jun. 2, 2009) 106(22):9051-9056.
Ulker, et al.; "T-DNA-mediated transfer of Agrobacterium tumefaciens chromosomal DNA into plants"; Nature Biotechnology (Sep. 2008) 26(9):1015-1017.
Yamane, et al.; "New Plasmid-Mediated Fluoroquinolone Efflux Pump, QepA, Found in an *Escherichia coli* Clinical Isolate"; Antimicrobial Agents and Chemotherapy (Sep. 2007) 51(9):3354-3360.
Yeo, et al.; "Tn5563, a transposon encoding putative mercuric ion transport proteins located on a plasmid pRA2 of Pseudomonas alcaligenes"; FEMS Microbiology Letters (1998) 165:253-260.
Yoshida, et al.; "Nucleotide Sequence and Characterization of the *Staphylococcus aureus* norA Gene, Which Confers Resistance to Quinolones"; Journal of Bacteriology (Dec. 1990) 172(12):6942-6949.
Zhang, et al.; "Disruption of the BMEI0066 gene attenuates the virulence of *Brucella melitensis* and decreases its stress tolerance"; International Journal of Biological Sciences (2009) 5(6):570-577.
Palanichelvam, et al.; A Second T-Region of the Soybean Supervirulent Chrysopine-Type Ti Plasmid pTiChry5, and Construction of a Fully Disarmed vir Helper Plasmid; Molecular Plant-Microbe Interactions (Jan. 1, 2000) 13(10):1081-1091.
Henkel, et al.; "Genome Sequence of the Octopine-Type Agrobacterium tumefaciens Strain Ach5"; Genome Announcements (Mar. 27, 2014) 2(2):1-2.
De Framond et al. "Mini-Ti: a new vector strategy for plant genetic engineering." Bio/technology 1.3 (1983):262-269.
Hoekema, A, et al. "A binary plant vector strategy based on separation of vir-and T-region of the Agrobacterium tumefaciens Ti-plasmid." Nature 303.5913 (1983): 179-180.
Ooms, G, et al. "Octopine Ti-plasmid deletion mutants of Agrobacterium tumefaciens with emphasis on the right side of the T-region." Plasmid 7.1 (1982): 15-29.

* cited by examiner

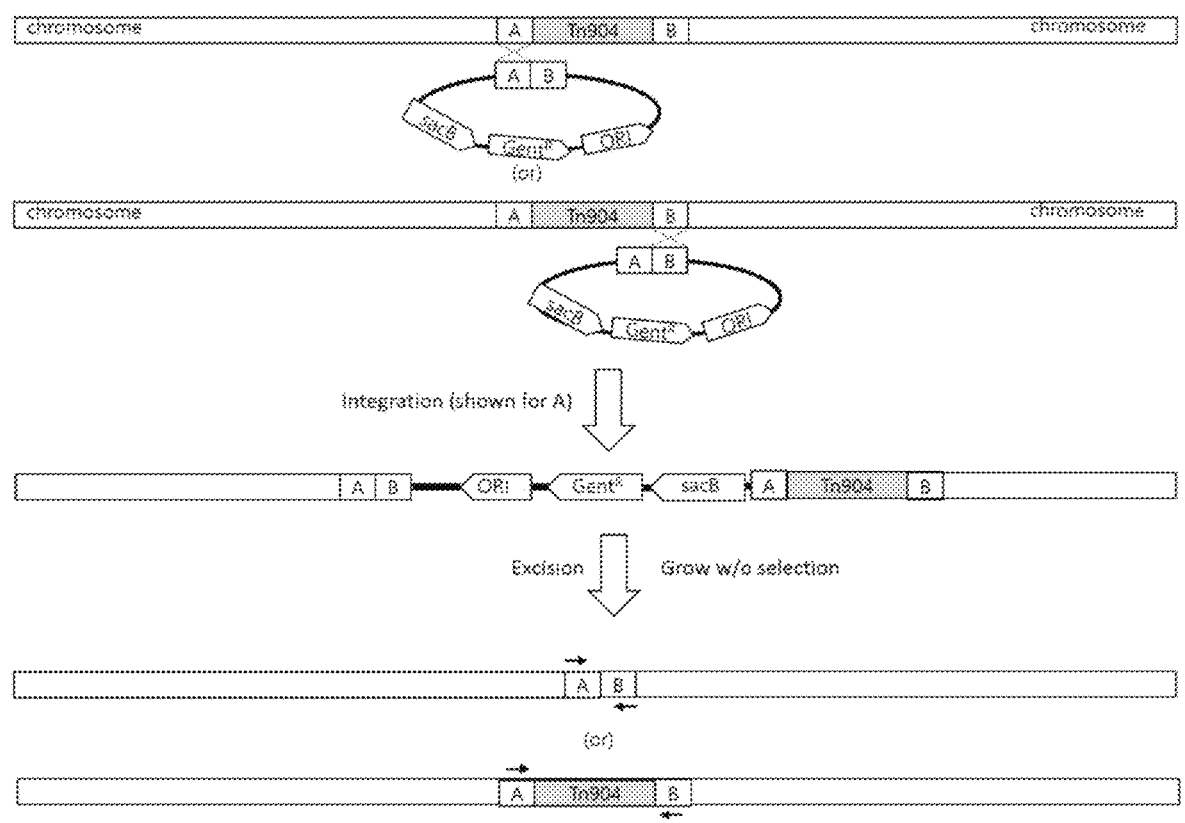

SEQUENCE LISTING

<160> NUMBER OF SEQ ID NOS: 9

<210> SEQ ID NO 1
<211> LENGTH: 23
<212> TYPE: DNA
<213> ORGANISM: Agrobacterium tumefaciens

<400> SEQUENCE: 1
gccagggttt tctgagatcc gtc                                              23

<210> SEQ ID NO 2
<211> LENGTH: 31
<212> TYPE: DNA
<213> ORGANISM: Agrobacterium tumefaciens

<400> SEQUENCE: 2
cactgttata atagctggat gcttgctgta c                                     31

<210> SEQ ID NO 3
<211> LENGTH: 25
<212> TYPE: DNA
<213> ORGANISM: Agrobacterium tumefaciens

<400> SEQUENCE: 3
tcagcatatg caacagattc agcac                                            25

<210> SEQ ID NO 4
<211> LENGTH: 27
<212> TYPE: DNA
<213> ORGANISM: Agrobacterium tumefaciens

<400> SEQUENCE: 4
ctttcctata gcaaggagg ctttctc                                           27

<210> SEQ ID NO 5
<211> LENGTH: 301
<212> TYPE: DNA
<213> ORGANISM: Agrobacterium tumefaciens
<220> FEATURE:
<221> NAME/KEY: misc_feature
<222> LOCATION: (151)..(151)
<223> OTHER INFORMATION: n is a, c, g, or t

<400> SEQUENCE: 5
cgcgaacccg ggcgcgcaag agcgcaaaag cggtcacagg cgacgttctg gcaaagctgc      60
ttgcgacttg cgagtcagac agcctgcgcg atctacgcga caaggcaatc ctgatggtgg     120
cctttgcctc gggcggccgg cggcgcagcg ngccccttta cggtgggatt cagagcttac     180
gttggttttt ggttccattg ctccccaaac cccgtaatcg aaccgccgat cgaggtgccg     240
gacggccctc ccctcccctc tttagccatt catcttggcc gcaccaaaac gacggccggc     300
g                                                                     301

<210> SEQ ID NO 6
<211> LENGTH: 301
<212> TYPE: DNA
<213> ORGANISM: Agrobacterium tumefaciens
<220> FEATURE:
<221> NAME/KEY: misc_feature
<222> LOCATION: (151)..(151)
<223> OTHER INFORMATION: n is a, c, g, or t

<400> SEQUENCE: 6
tagaatgttt ccctcggctg cgacgaccag gcgctcggga tatatccgca ggctgacggg      60

| | |
|---|---|
| ccggtttgca aatgatgcag gcacgctgta gcggttccgc tcgaaggtaa tcaggcatgt | 120 |
| tggtgagacg cgcttgctct gctcgacgaa ngcccctta cggtgggatt cagagcttac | 180 |
| gttggttttt ggttccattg ctccccaaac cccatatggg cgttgtcgcg gagatcgctg | 240 |
| atcgggttct tgtgatgcgc gggggccagg tggtcgagtc cggtccagtg gatagcgtgt | 300 |
| t | 301 |

<210> SEQ ID NO 7
<211> LENGTH: 11762
<212> TYPE: DNA
<213> ORGANISM: Agrobacterium tumefaciens

<400> SEQUENCE: 7

| | |
|---|---|
| agatcgccgg actgcggatt gaacagttgg taatggggtt tggggagcaa tggaaccaaa | 60 |
| aaccaacgta agccctacca acgcttttcg gtgtcttctt cccaggcgcc catctcgaca | 120 |
| aaacagttgc gcatgtcggc ctcctggctg atctcggtca gcaggtcatg cacgctcttg | 180 |
| tccagctcat cgtcgctccg atacggaatg gtcaactcat agtggccggc atccagccgc | 240 |
| ttcatgccat agggctccag gcagtagcgc tcaatgttct ccgtggcccg cttccggccg | 300 |
| cgcacgaact tgctgttatt caccaccgcg aggcgcaggg tgacggtggc cacccgctcg | 360 |
| gcggcgggcg gctctgccgg cgacgcggcc gaaggctgct ggtcgcgtga cctggcgctc | 420 |
| ttctggtacg cgccgatctc gacaccacgg tggcgcaggt agctgtacag cgtgctcttg | 480 |
| gagatgtgca gcttctcgcc gatcgcgctg acgctcaggc gaccttcgcg gtagagggtt | 540 |
| tcggccgcca tggcggtggc ctcagccttg gctggcaggc ccttgggacg gccaccgatc | 600 |
| cggccacgcg cccgtgcggc cgacagaccc gcctgagtcc gctcgcggat cagctcgcgc | 660 |
| tcgaactccg ccagcgaggc gaacaggttg aacaccaggc ggccttgggc gtgggtggtg | 720 |
| tcgatggggt cattcaggct ctgtaagccg accttgcgct ctgccagctc gccgaccaac | 780 |
| tcgaccaggt gcttgaggga acgcccaagg cgatccagct tccagatcac cacggcatca | 840 |
| cccggccgca cgttggccag cagtttgtcc aactccggcc gggcgctttt cgcgccgctg | 900 |
| gcgatgtctt ggtagatgcg ttcgcacccg gcctgtttca gggcatcgac ttgtaggtcg | 960 |
| gctttctgat cccgagtgct cactcgcgca taaccgatct tcatcaaaag tactgtttac | 1020 |
| tcgactacgt tagtaatagt tgaacttttga ttaagcgtac cagttatttg aaccgtagcg | 1080 |
| cggggagctt aacgaaccgg ggtcgtttgc gggagagggc gaaatcctac gctaaggctt | 1140 |
| tggccaacga tattctccgg taagattgat gtgttcccag gggataggag aagtcgcttg | 1200 |
| atatctagta tgacgtctgt cgcacctgct tgatcgcggc cgcgatagct agatcgcgtt | 1260 |
| gctcctcttc tccatccgcg ttccaagctg cggaaaggca cccataagcg tacgcctggt | 1320 |
| cgagcaggcg acgcggatcg acgtccagcg cacgagagaa tgcgtccgcc atctgtgcaa | 1380 |
| tgcgtctagg atcgagacaa aggtcgtctc tgtcagccgg atcgtagaac atattggcgg | 1440 |
| cgccaaagcc cacttcaccg accagaccga cgggatctat caccagccag ccgcgactgg | 1500 |
| agaaacatgat gttttcatga tgcagatcgc catgtagccc acgcagttcc gaggcattgc | 1560 |
| tcatcatttg atcggctata atcgccgcgt ggacgtagtc agtttgacaa cctgcgtttt | 1620 |
| gatcatcgcg cgcccgctga aacaaagctg caaagcgatc ccggatcggg agaagggcag | 1680 |
| aaggcagggg ttcctcagat gcggcataca gcttcgccat tagttccgct gcaatttcgg | 1740 |
| tcgcctggta gtcgccgtgc tcggcaacga tgtgagagag cattcgctcc ccggcatatt | 1800 |

```
cgagcaacat cagattgttc tcacgaccga gcaaccggac tgctcccctc ccattgcgcc    1860
ataccagata gtcggccccg cgcagttcat cagcaatgtc ttctataggt ttcaatccct    1920
tgacgattgc aggagtcccg tctggcaatg aaactttcca acgaggctg  gaaaaggtgt    1980 ccgcaatgag aacaggttgc gaaacgtgcc aatgagcagg aaaaacaggc ggcatgaaca    2040
tcaaccccaa gtcagagggt ccaatcgcag atagaaggca aggcgttcgc ggtcggggc    2100 ttcgatcccc aatacattga ataggacagc gaaggcgcgc tctgcttcat ctggcgctgc    2160
ccagttctct tcggcgttag caatcatgag tgccaaatcg gcatagcgat ctgctgttcc    2220
gagccgccca aggtcgatca gacccgtgca ttgaagagtt ttagggtcca ccatgaagtt    2280
cggcatgcag ggatcaccat ggcaaacaac catatcggtg cgctcttggt cgagccgcac    2340
cggtagctct cgttcgacac gagccaaaag atcgagctgc ggcgtactct tgtcctcgtc    2400
cggtaagaag tcgggattga cggcattgcg ggacaccaca tcaacggcgc gtccgaacat    2460
tcgcgacagc ctgcgctcaa acggacattg atcaaccgat aggctgtgaa cagcgccaag    2520
ttgctgcccc attgacggcc acgctttgag caaatccgct ccagacagat cagccgccgg    2580
tactcccgga attgccgtta tcaccaagca tgcaccctcc tgttcctcct gccagttgat    2640
cacctcgggg caagccacac ctcgaccttt gagccaaatg aggcggtcac gctctccagc    2700
gagctcaccg cggcgggaag caggtgcgat tttcgcgaag gcatgcccgt caccacgtcg    2760
aaaaacaaaa tcaccagatt ctccgcctct gacaggcaac cagtcagaat gcgattcacc    2820
aaaaaaaata ttagttcgat tcaatggagg ttccttcagt tttctgatga agcgcggagg    2880
tggctcaacc tgcgaaaaga aacgagttgc tacgtaagtc cgagaacatg ctttccatgg    2940
tctctgagct cgcctttggg accgacatat cggtagagag tgacgcgctc gatgccgagt    3000
tccttgcaga gatcggaaac tgaagtatcg cgctgggcca tggcggcttg cgcgagacgc    3060
acctgagctt tggtgagcgc gaattttcgt ccgcccttgc gaccgcgcgc tctcgcggag    3120
gcgagacccg ccatggtgcg ctctcggatc agatcccgct cgaactcggc caaggtggcg    3180
aagattccga acaccatgcg accggacgca gtcgtggtgt cgatctgagc gcccttttcca   3240 gtcagaaccc gcaggccgat cttgcggtct gacagctcct tcaccgtgtt gaccagatgg    3300
gcaagcgatc gtccgaggcg atcgagcttc cagaccacca gcacatcgcc gtcacgcaat    3360
gacttgaggc aggcagtcaa gccagggcga tcatcacgac cgccggaagc aagatcatca    3420
tagatattgt cccgttcgac acctgcggcg cgcaaggcgt cgtgctgcag gtcgagagac    3480
tgcgagccat cggctttgga gacgcgggca tatccgatca gcatgtatca caaacgttgg    3540
tttgaggcgg cgcttcggcc acgattgcat tgacctctgg aaatgtatct caaccagctt    3600
cataaacaaa gcgtcttgaa cgctatcaga ttttgaaaaa ggaacatgta tgccgcgtcg    3660
cgtcactcta accgatcggc agaaagacgc gctgttgcgc ttgccgactt cacagacgga    3720
tttgctcaag cactatacgc tgagtgatga agaccttggg catatcaggc tgcgtcggcg    3780
cgctcacaac aggttcggct tcgccctgca attgtgtgtc ctgcgctatc ccggccgggt    3840
gctggctcca ggcgaactga tccctgcaga ggtcatcgaa tttatcggag cgcagcttgg    3900
cctgggtgcc gacgatctcg tagactatgc tgcccgcgag gaaacacggc acgagcatct    3960
tgccgagtta cggggctct acggcttccg caccttctcc ggacgtggtg cgagcgagct    4020
gaaggaatgg ttgttccgag aagccgagat ggcggtgtcg aacgaggata tcgcccgtcg    4080
cttcgtagcc gagtgccgac gcacccgcac tgtccttccc gcgacatcca cgatcgagcg    4140
gctttgtgcc gcggctctcg tcgatgccga gcgacgcatc gagacgagga tcgccagtcg    4200
```

```
gctgcctatg tcgatccgag aacagttgct ggcattgctc gaggagacgg ctgatgatcg    4260
ggtgacccgt tttgtgtggc tgcgccagtt cgagcctggc tcgaactctt cgtcggccaa    4320
ccggctgctc gaccggctcg aatatctgca acgcatcgat ctccccgagg atctgcttgc    4380
cggcgttcct gcccatcggg tgactcgtct gcgcaggcag ggtgaacggt attatgccga    4440
cggcatgcgc gatctcccgg aggacaggcg gcttgcgatc ttggctgttt gcgtctcgga    4500
atggcaggcg atgttggccg acgcagtggt cgaaacccac gaccggatcg tcggccgtct    4560
ctaccgtgct tcggagcgta tttgccatgc aaaggtcgca gacgaagcgg gggtggtgcg    4620
tgacaccctg aaatccttcg ccgagatcgg gggcgccctg tcgatgcac aggatgatgg     4680
ccagccgctg ggcgatgtca tcgcgagtgg gtcagggtgg gacggcttaa aaacccttgt    4740
tgcaatggca accaggctga ccgccaccat ggccgacgat ccgctcaatc atgtgctcga    4800
cggttatcac cgcttccgcc gatacgctcc acgcatgttg cgcctgctcg atctgcgagc    4860
tgcgcccgtt gcactgccgc ttctggaagc ggtgacggcc cttcgtaccg gtttgaacga    4920
tgccgcgatg accagcttct tgcggcccag ctcgaaatgg catcgccacc ttcgggccca    4980
gagggctggc gacgctcgcc tatgggagat cgcggtgctg ttccatctgc gcgatgcgtt    5040
ccgctccgga gatgtctggc ttactaggtc ccggcgctat ggcgatctga acacgcact     5100
cgttccggca caatccatcg cggaaggcgg tcgtctcgct gtgccattgc ggccggagga    5160
atggctggca gaccggcaag ctcgcctcga catgcggttg cgcgagcttg gccgtgccgc    5220
tcgcgcaggc acgatcccgg gcgggtcgat tgaaaacggc gttctgcata tcgagaaact    5280
cgaagccgcc gcgccgacag gcgccgaaga tctggtgctc gatctctaca agcagatccc    5340
gcccacgcgc atcaccgatc tcctgctgga ggtggatgcg gcgaccggct tcaccgaagc    5400
gttcacccat ctgcgcacag gagcaccctg cgctgaccgg atcgggctaa tgaacgttat    5460
cttggcggaa gggatcaacc tcggcttgcg caaaatggcg gatgcgacaa cacccacac     5520
cttctgggaa ttgatccgca ttggacggtg gcatgtcgag ggcgaagcct atgaccgggc    5580
gctggccatg gtggtcgagg cacaggcagc gttacccatg gcccggttct ggggcatggg    5640
cacgtcggct tcgagcgacg gacagttctt cgtcgctaca gagcaaggtg aggccatgaa    5700
cctggtcaac gcgaaatatg gcaatacccc gggcctgaaa gcctatagcc acgtctccga    5760
ccaatatgcg ccgttcgcaa cccaggtgat tcctgcaacg gcaagcgaag cgccttacat    5820
cctcgatggc ctgctgatga acgatgctgg acgccatatc cgcgagcagt tcaccgacac    5880
gggcggcttc accgatcacg tctttgccgc atgtgccatt ctcggctacc ggttcgctcc    5940
gcgcatccgc gacctgccat ccaaacggct ctacgcgttc aatccgtcgg ccgccccggc    6000
gcacctgcga gcgttgatcg gcggaaaggt caaccaagcc atgatcgagc gcaattggcc    6060
cgacatcctg cgcatcgccg ccaccattgc tgccgggacc gtcgcgccaa gccagattct    6120
gcggaaactc gcctcctatc gcggcagaa cgagctcgcg acagccctgc gggaagtcgg    6180
tcgcgtcgag cgcaccctgt tcatgatcga ctggattctg gatgccgaac tccaacggcg    6240
tgcccagatc gggctcaaca aaggcgaagc tcatcatgcg ctgaagcggg caatcagctt    6300
ccaccgccgc ggtgaaatcc gcgaccgttc cgccgaaggc cagcattacc gcatcgccgg    6360
catgaatctg ctcgccgcca tcatcatctt ctggaacacc atgaagctcg gcgaggtcgt    6420
tgcaaaccag aaacgcgatg gaaagctgct atcgcccgat ctcttggccc atgtttcgcc    6480
gctcggatgg gaacacatca atctcaccgg agaatatcgc tggccaaagc cttagcgtag    6540
```

```
gattccgccc cctcccgcaa acgaccccca accgagccat tcctcgatag agttcggcaa    6600
aaccttcgtt ttgtcgaacc attgcatcgc cctttgtgat tggcgtataa acacacaaac    6660
acctattagc ggagaacgct atgaatacca ttcgctggaa tgtcgccgtc tcggccgaca    6720
ccgaccagtc gcttcggatg tttctggcca gccaggcgg cggccgtaag ggcgacctgt     6780
cgcgcttcat cgaagaagcg gtacgggcac acatcctgga gctgagcgct gagcaggcca    6840
aggccgctaa cgcccatctg agtgaggcag aattgaccaa cgcggttgac gaagcgctcg    6900
actgggcacg taagcgctga tgcgggtcgt gttggatacc aacatcctgt tcagcgccct    6960
gatctcgcca catggcgcgc ccgatgcgat ctaccgtgcc tggcgggcgg cgcgtttcga    7020
ggtggtgacc tcgcggatgc aactcgatga aattcgtcga gccagccgct atcccaagct    7080
tcaggccatc ctacagcccg ccaaggtggg cgccatgatc aataacctgc aacgggctgt    7140
ggtactggag cgcctgacca tcgaggtcga agccgatgat ccggatgact cgttttttgct   7200 ggccatggcc ttggcgggcg atgcggacta cctggtaacc ggtgatcgcc gcgccggcct    7260
gctgcaacgc gggcacatcg aacgcacgcg gatcgtcacg cccgccgtgt tctgcgtcga    7320
ggtgctgtga tcaatgccgg tcggttttct gactcaagag caacgcgacg gttttggccg    7380
ctatgttgat tcgcccagcc gtgaagagct ggaacgttac ttccacctga gcgatgaaga    7440
ccgtgaagcc atccaggtgc tgcggggtaa ccataaccgt ctgggttatg ccgttctgct    7500
gaccaccgtc cgcttcgttg gcgttctgcc ggacaagccc gccgccgtgc cggtggaagt    7560
cctgcaggtg ctttgccgac aactggcgat tccagacccc gactgcctcc agcgctatag    7620
cgatcatcgc cgctggatac atgccaccga tattcagaac cgctttggct atcgtcattt    7680
caccgatccg ggcatcggct ttcgcttgag ccgctggctg tatgccctct gctggacggg    7740
caccgaccgg ccgggagtgc tgtttgagcg agccacctcg tggctgttca cacagaaagt    7800
cctcctgcct ggtgtgtctc aactagagcg cttatcgcc cagttgcgca gtcgggtcga    7860
agaacgcctc tggtttacgc tgggccgcag cgtgactgag gaacagcgat tgcaactgca    7920
agacttgctg acggtggccg aaggcaaccg cagctcccgg ctggatcaat tgcgctccgg    7980
cccggtcatg gtcagtggcc ccgcgttgat tcgggcactg cgccggctcg atgacgtgcg    8040
cggcatcggc atcaccttgc cggcggcggc gcacatccct cccagccgta tcgccgccct    8100
ggcccgcttc gccaacacgg ccaaggtcac cgcgattaat cggctgccgg cgtcgcggcg    8160
gatggcgaca ctggtggcct tcgcactctg cctggaggcg actgcgcacg acgacgcact    8220
ggaagtcctg gaggccttgc tgcgcgacct gttcagcaac gcggagaagg ccgacaagaa    8280
agcccgcatg cgcagcctga aagacctgga tcggtcggcc gcgacgctcg ccgccgcgtg    8340
caaggtcgtg ctggacagct cgatcagcga tgacaacgtg cgcgcccggc tgttcaacga    8400
cctgccgagg accaccctgg aaaaggccct ggaagaggtc aacgcgctga tccgcccggt    8460
agatgacgtc tattttcttg cattggaagc gcgctaccgc agcgtgcgcc gcttcctgcc    8520
cgacctgctc aagcacatcc gcttcggctt cagcccggcc ggcaagggcg tggcggctag    8580
tctggagtgg ctgcaactga acctgccgcg ccggaagcca gaggatgacg cgccgcagga    8640
gatcgtggcc aaggcttggc agaagcacat caccccgcgaa gatggctccc tcgacatggg    8700
tgcctatgtg ttctgcacgc tcgatgcgct gcgcacggcc ctgcgccgcc gcgatgtctt    8760
cgtctcgccc agttggcgct atgccgaccc gcgccttggc ctgctcgacg gtgccgaatg    8820
gctggcggcg cgaccgatca tctgccggtc actgggcctg accatcgacg ccaaaaccac    8880
cctggacgcc ttgtccgtcg agctggatgc aacctggctg gcagtagccg cgcgcctgcc    8940
```

```
cgacaacccg gcgattcaac tgagcgagaa caccgagggc aagaccgaac tgtcgctcgg      9000
ggcgctggac aagctggacg agccctgctc gttgctgcaa ctgcgggcgg ccgtgtctga      9060
cctgatgccg cgtgtcgatc tgccggaaat cctcttggaa atcgccgccc gcactggctt      9120
ttccgaggcc ttcacccatg tctccgaacg caatgcacgc gccgacaacc tggtcaccag      9180
cctctgcgcg gtgctgttgg gcggggcctg caacaccggc ctggagccct gatccgcac      9240 cgacaacccg gcgctgcgcc gtgaccggct gtcctgggtc agccagaatt atatccgcga      9300
cgacaccctg tcagcggcta acgccatcct ggtcggagcg caaagccaac tggaactggc      9360
ccaagtctgg ggtggcggcg aggtcgcctc cgccgatggc atgcgcttcg tcgtaccggt      9420
gcgcaccgtg catgccggcc ccaatccgaa gtatttcggc accggccggg tgtcacctg      9480 gtacaacctg atttccgacc aattctccgg cctcaacgcc atcaccgtgc ccggcacgct      9540
gcgcgacagc ctggtgttgc tggcggtcgt gctggaacag cagaccgagt tgcagccgac      9600
gcaaatcatg accgacaccg gggcctacag cgatgtggtg ttcgggctct ccgcctact      9660 tggctaccac ttcagtccgc ggctggccga tgtcggcggt acccgcttct ggcgcacgcg      9720
cccggacgcg gactacggca agctcaacgg gctggcccgc cagtcggtca aactcgacct      9780
gatcgccgag cactgggacg acctgctgcg cctggccggc tcgctcaaac tcggccgggt      9840
gccggcgact ggcatcatgc gcacgctgca aacgggagat agaccacccc ggctggccca      9900
ggcgctggcc gaattcgggc ggatcgaaaa gactctgcac acgttgacct atatcgacga      9960
cgagtccaag cgccgcgcca ccctgaccca gttgaaccga ggcgaaggcc ggcacagcct     10020
ggcccgcgcc gtgttccacg gcaaacgcgg cgagctccgc cagcgctacc gcgaaggcca     10080
ggaagaccag ctcggtgctc tgggcctggt ggtgaacatc atcgtgctgt ggaacacccct    10140 ctacatgacg gcggccgtgg aacggctcaa gcagcacggc tatccagtgc tggaagagga     10200
tttggcccgg ctatcgccgc tgatctacga gcacatcaac atgctcgggc ggtattcctt     10260
tgcggtaccg gaagaagttg cgcgcggcga gctgcggcca ctgcgtaatc cagacgacga     10320
cctgtgatcc ccctaaacgc tatgagcaac cccaagctg ctgctggatc ggcgggcact      10380
tcaccgagcc gaacgaacag aaaacgcagc aatcccctgg gttggggcgc agcagcgcct     10440
tgcagttgct gcactcgtaa tagaactggc aggcgtccgt gggcatggtt tccggcttgg     10500
cgaagccgca gcgcgggcaa gtcagcacgg actcaaggac aatggcgctc atcgtgacct     10560
cacttctgca ctgtggaggg gtatcccgcg ttcgcggtcg cctcagtcag tgcctcgggc     10620
tgggccttat cgggatcgta ggtgacggtc gccgtcttct ggtcgaaatt gacctggacg     10680
tcactcacgc cggacacctt ctccagcgac ttcttgaccg tgatcggaca gagtccgcac     10740
gtcatgttct gcacgtcgag cgtgacggtt tcggggggag ccgccagcgc cacgaagggc     10800
aaggcgaaaa gcacggcgat cagcagtttg cgcatggtta atctccttca gtagaacagc     10860
ggggcgagcc acggcacggc caataggccg agcagcagca cgctgacgat ccagaacacg     10920
agtcgctgtc gcacgagcgt gcgcggatcg gcgcagggtg tacctggcgt acaaacctgt     10980
ggcaccaggt agagcttgcg gaatgccaat cccaggaaca gtagagtcaa cccgatgaag     11040 aggggggcgta gtggctccat catggtcaga gcgcccaccc acgtaccgcc gacaccgagt     11100
gccaacagca ccagtggccc gacacagcac accgacgcac cgatggcggt cagcgaactc     11160
gcgaccagca agccttttccc ggtgagttgc atccccattc ccatctcctg agcctgattg     11220
cctaggtgct attctaaact ccgtaccaaa gtacggaatc aaggagaaag tgatggccac     11280
```

```
agagctgacc attggcaagc tggcagacgc cgccggggtg aacgtcgaga cgatccgcta    11340
ctaccagcga cgcgggctgc tggatgaacc agccaaaccc ttgggtggcc atcggcgcta    11400
tccggtggac atggtgaagc gactgcgttt catcaagcgg gctcaggcgc tgggtttcac    11460
gctctcggaa gtcggtggac tgctgacgct ggatgagtcg tgcgcctgtg ccgaaacgcg    11520
agcacgggct gcacgcaagc tcgcgttgat cgagcagaag atggccgact tggtcgtcat    11580
gcagcaactg ttaggcgaac tggtgcagca atgtgatgcg ggagacgcg gaacgatctg    11640 cccgatcatc gaggcactga tcagagagta atgcctggcg ggtgagctgg agatcggaaa    11700
gcccctttac ggtgggattc agagcttacg ttggtttttg gttccattgc tccccaaacc    11760
cc                                                                    11762

<210> SEQ ID NO 8
<211> LENGTH: 7733
<212> TYPE: DNA
<213> ORGANISM: Artificial Sequence
<220> FEATURE:
<223> OTHER INFORMATION: Allele-replacement vector for At chromosomal
      Tn904 copy

<400> SEQUENCE: 8
gtttagataa ttccccaagc ccgaaacctc ccctccccg tcatctcccg caaccccagc       60
tccaaaataa tccgccgcgc cgcctgcggc gtcacatcga gcgtcttcgc caccattttt     120
gccgacacca acggtttggc catcaccaac tcaaccagct ccggcagttt tgaagatgtc     180 cggcgcccctt ccagcttccg ctcgaacagt gtccgggcaa acgccagccg gtcatgttct    240
ttcaatccga tctcggcggc cgcgatcagt ccgtgggcga tggccagcat ccgggtttcc    300
cggtcgcgat gccgacgacg atcgactgga atggatttca ggccggtatt gatggcggcg    360
agatgggcac cggtggtaac gccggtctgg cgcaatatcg acgcggccag cggccggcca    420
agccagggcg catgctgaag gacgacagt tcgttccagg catcgagggc aatgatggcc     480
tgcagcaccg ccggcaagtc ttgcgtttgt cgcaacacgc ttcgccattc ttccagccgg    540
gcgtcctcgt cccagtccag atcgtagatc atcggatctt tctcttggcc gccgccacgg    600
ccaggccgtg ttgcattctc gatcgccgct tccgatcggg ccagcaccgc atcgatagcg    660
gcataatcga tgccggggag atgttcgatg tcgtcggcgt cttcccccctc gccttccgga    720 tcgttcgcga ccgcgcgccg gatggcatca gcgggcgtcg cctcgtcagc gttgactgac    780
gtgatctccg aggttttttcg cagtgtccga agtccgtcgg ccgatagcgc ccagccaggc    840
aactggccag caatgcgccg acgcgtgcgc aggacgtcgc gggcgatggt cagctcgtgg    900
gtgggtgtgc gaatatctct gacatggtcg tggaggacga ggtcttcgag atggacgagt    960
tcgccgtcga tccacagcga ggcgcaggca tcggtgaact gggtgcgttc gacgaagccc    1020
tgcccgaccg gtgaacgggc gatacgctcg tccagacgcg taagcgcgat accggcgtcg    1080
aaagccggcc gcatcagggc gctcatgctg atttttgcga gatcgtaagc cattgaaatc    1140
atggtaaatg agttcttaaa cgaactctat caaaatattg cggttcctca catggtatga    1200
ttggtagttg aacttctaac catcgataag tacctcttat caatggtagt tgatttcgcg    1260
gcgcaaatcg aggaaaatcg gggcaaatca cggtcccagc ggccgccgaa acctgcgatt    1320
ctggagcctc tcgtggctaa agcgaagaca tcacagacgt ccgtcgagcg gcgcgccgaa    1380
gagctcgata ccattgcgtc cgtcctgccg ctcgaacgcc gcgacgagct cgccgagctg    1440
ttgaccgatc aggacatcga gacgctgcgc catctcgtta atcagggcat gggcgacaat    1500
```

```
acgttgcgcg cacttacatc cgacctcgct tacctcgaag cctgggggtt ggcgaccacc      1560
ggcagttctc ttccctggcc cgcaccggaa gcactactgt tgaaatttgt cgcccatcac      1620
ctctgggatc cggaaaagcg cgcaacagat cccgaccacg gcatgccagc tgcggtcgat      1680
gaaaacctcc ggcgccaggg ttttctgaga tccgtcggcc cacacgcacc atcgacggtg      1740
cgccggcggc tggccaactg gtcgacgctg accaggtggc gcggcctcca tggcgccttc      1800
gcctcccctg cccttaaatc agccattcgt ctggccgtgc gcgccgttcc gcgaacccgg      1860
gcgcgcaaga gcgcaaaagc ggtcacaggc gacgttctgg caaagctgct tgcgacttgc      1920
gagtcagaca gcctgcgcga tctacgcgac aaggcaatcc tgatggtggc ctttgcctcg      1980
ggcggccggc ggcgcagcgg ccccctttacg gtgggattca gagcttacgt tggtttttgg      2040
ttccattgct ccccaaaccc cgtaatcgaa ccgccgatcg aggtgccgga cggccctccc      2100
ctcccctctt tagccattca tcttggccgc accaaaacga cggccggcga gcaggacaac      2160
gtcgtctatc tcacaggccg gcctgtcgag gcgttgaatg cctggctggc ggccgccagg      2220
atcgacaagg gcagcgtgtt tcgcgggatc ggaaaatggg gaacggtttc caaacgggcg      2280
ctagatccac agtcggtcaa tgcaatcatc aagcagcgcg ccgaaatagc agggttggag      2340
gcaggccagt tttcggcgca tggtctgcgg tcgggctatc tgaccgaagc ggccaaccga      2400
ggcattcccc tccccgaggc gatggagcaa tcacgccacc gatcggtaca gcaagcatcc      2460
agctattata acagtgctac acgcagaagc gggcgagcgg cccgattgtt gtagatcggg      2520
tcccctgtca gaattgccag ggcgagatca attcgagccc tgttgtctcg aaatctttga      2580
ggtttcgggt cgccaaccgg ccaccattga tccgcgctat cgccgcgatc aagccgtcgg      2640
agccgacatc cccctcccct gccgcgcagc gtctcccatg atatcgccat aggccaatgc      2700
tgcttcttcc gtgaaggcaa acatcttgtc ggagaaccgg cgacgccagc tcacaagtcc      2760
ctcttccagg cgatcggcgc gctgatccgg cctgatcttt tgaataccaa aagcgatctc      2820
agcaactgca accgtcggca atgccaattc ggcgtcgtga cgaaccagcc atgctatgac      2880
tgcagaatcg ggagctttct tcaaagtctc cggcatcaca ttcgtgtcga gaaaaatcaa      2940
agctcgacgc ttttgtgagc gcgtctgttt tcatcgatga tactgtcgaa atcgatatcc      3000
gtacccgact gcgatgaaag acgactatag aatttcgcag cgggttcacg tcctgcctca      3060
cgagcctcat aggttttgag cgcgcgctcg acgatatcgg caatcgtgcg attttctcgg      3120
cgggcgagct tatgggcgag gtcgcgcgct ttggaactgc ggacggatag ttgcggtgtt      3180
accattgagt gctcctttct ctggatccac agtaacttaa attgaaatag ccatcgagaa      3240
ggcatctgcc atctcgatgg ctatttagta ttgctgattt ggcgcccgt ggtttggcca      3300 tcgttcatgt tcgttccgcg tggaggccaa cacatcccct ccccgaacac cacactttaa      3360
gcaatttccg ccgtggacgg ccatcagagc gtatttcaag caggtcgtgg cccggatgtc      3420
gttcgacgcc gcgttttgcg tctgacaggg ctgcattcag gtcataaaac acgcttgcaa      3480
ctactcattt tcttacgcat tccttatttg tacaaagcac ctgaaaaacg cacgagagaa      3540
ccatagcaaa acggcaagtc gccaatccat cgccggcgcc taaacgcctt ataggctatg      3600
cacgtgtctc taccgacgat caggtccatg acgctcaaat ggacgagctg cgtgctgccg      3660
gctgcgagca gatatttcag gagcaaggct cgggtgcatc acgcgctcgg ccggttctca      3720
caagacttct cggggacctc accgccggcg acgtgctggt tgtcgtccgg ttggatcgcc      3780
ttgcccggtc tgtcagccac cttctgcaag tgatcgaaga tctcgaggag cgtggtgtcc      3840
attttcgttc gatctgcgat ccgatcgata cgtccacgcc acagggcatg ttttctctcc      3900
```

```
aggttcttgg cgagcgaata gctgcagtcg cgcactgaga aatcctccat gccgaccggc   3960
aaggcgatgc gcttcgagaa gctctggaaa atatcttcgg ccgcggatcg atccttttta   4020
acccatcaca tatacctgcc gttcactatt atttagtgaa atgagatatt atgatatttt   4080
ctgaattgtg attaaaaagg caactttatg cccatgcaac agaaactata aaaatacag    4140 agaatgaaaa gaaacagata gatttttttag ttctttaggc ccgtagtctg caaatccttt  4200
tatgattttc tatcaaacaa aagaggaaaa tagaccagtt gcaatccaaa cgagagtcta   4260
atagaatgag gtcgaaaagt aaatcgcgcg ggtttgttac tgataaagca ggcaagacct   4320
aaaatgtgta aagggcaaag tgtatacttt ggcgtcaccc cttacatatt ttaggtcttt   4380
ttttattgtg cgtaactaac ttgccatctt caaacaggag ggctggaaga agcagaccgc   4440
taacacagta cataaaaaag gagacatgaa cgatgaacat caaaaagttt gcaaaacaag   4500
caacagtatt aacctttact accgcactgc tggcaggagg cgcaactcaa gcgtttgcga   4560
aagaaacgaa ccaaaagcca tataaggaaa catacggcat ttcccatatt acacgccatg   4620
atatgctgca aatccctgaa cagcaaaaaa atgaaaaata tcaagttcct gaattcgatt   4680
cgtccacaat taaaaatatc tcttctgcaa aaggcctgga cgtttgggac agctggccat   4740
tacaaaacgc tgacggcact gtcgcaaact atcacggcta ccacatcgtc tttgcattag   4800
ccggagatcc taaaaatgcg gatgacacat cgatttacat gttctatcaa aaagtcggcg   4860
aaacttctat tgacagctgg aaaaacgctg gccgcgtctt taaagacagc gacaaattcg   4920
atgcaaatga ttctatccta aaagaccaaa cacaagaatg gtcaggttca gcccacattta  4980 catctgacgg aaaaatccgt ttattctaca ctgatttctc cggtaaacat tacggcaaac   5040
aaacactgac aactgcacaa gttaacgtat cagcatcaga cagctctttg aacatcaacg   5100
gtgtagagga ttataaatca atctttgacg gtgacggaaa aacgtatcaa aatgtacagc   5160
agttcatcga tgaaggcaac tacagctcag gcgacaacca tacgctgaga gatcctcact   5220
acgtagaaga taaaggccac aaatacttag tatttgaagc aaaacactgga actgaagatg   5280 gctaccaagg cgaagaatct ttatttaaca aagcatacta tggcaaaagc acatcattct   5340
tccgtcaaga aagtcaaaaa cttctgcaaa gcgataaaaa acgcacggct gagttagcaa   5400
acggcgctct cggtatgatt gagctaaacg atgattacac actgaaaaaa gtgatgaaac   5460
cgctgattgc atctaacaca gtaacagatg aaattgaacg cgcgaacgtc tttaaaatga   5520
acggcaaatg gtacctgttc actgactccc gcggatcaaa aatgacgatt gacggcatta   5580
cgtctaacga tatttacatg cttggttatg tttctaattc tttaactggc ccatacaagc   5640
cgctgaacaa aactggcctt gtgttaaaaa tggatcttga tcctaacgat gtaacccttta  5700 cttactcaca cttcgctgta cctcaagcga aggaaacaa tgtcgtgatt acaagctata    5760
tgacaaacag aggattctac gcagacaaac aatcaacgtt tgcgccaagc ttcctgctga   5820
acatcaaagg caagaaaaca tctgttgtca aagcacgcat ccttgaacaa ggacaattaa   5880
cagttaacaa ataaggccgg cctcgcgaat gcatctagat ccaatccaat atgcatggca   5940
tgccgaatcc atgtgggagt ttattcttga cacagatatt tatgatataa aactgagta   6000 agcttaacat aaggaggaaa acatatgtt acgcagcagc aacgatgtta cgcagcaggg   6060
cagtcgccct aaaacaaagt taggtggctc aagtatgggc atcattcgca catgtaggct   6120
cggccctgac caagtcaaat ccatgcgggc tgctcttgat cttttcggtc gtgagttcgg   6180
agacgtagcc acctactccc aacatcagcc ggactccgat tacctcggga acttgctccg   6240
```

```
tagtaagaca ttcatcgcgc ttgctgcctt cgaccaagaa gcggttgttg gcgctctcgc   6300
ggcttacgtt ctgcccaagt ttgagcagcc gcgtagtgag atctatatct atgatctcgc   6360
agtctccggc gagcaccgga ggcagggcat tgccaccgcg ctcatcaatc tcctcaagca   6420
tgaggccaac gcgcttggtg cttatgtgat ctacgtgcaa gcagattacg gtgacgatcc   6480
cgcagtggct ctctatacaa agttgggcat acgggaagaa gtgatgcact tgatatcga    6540 cccaagtacc gccacctaat aatgtctaac aattcgttca agccgacgcc gcttcgcggc   6600
gcggcttaac tcaagcgtta gatgcactat acgtaccaat ccaaatcgga tcccgggccc   6660
gtcgactgca gaggcctgca tgcaagcttg gcgtaatcat ggtcatagct gtttcctgtg   6720
tgaaattgtt atccgctcac aattccacac aacatacgag ccggaagcat aaagtgtaaa   6780
gcctggggtg cctaatgagt gagctaactc acattaattg cgttgcgctc actgcccgct   6840
ttccagtcgg gaaacctgtc gtgccagctg cattaatgaa tcggccaacg cgcggggaga   6900
ggcggtttgc gtattgggcg ctcttccgct tcctcgctca ctgactcgct gcgctcggtc   6960
gttcggctgc ggcgagcggt atcagctcac tcaaaggcgg taatacggtt atccacagaa   7020
tcaggggata acgcaggaaa gaacatgtga gcaaaaggcc agcaaaaggc caggaaccgt   7080
aaaaaggccg cgttgctggc gtttttccat aggctccgcc ccctgacga gcatcacaaa    7140 aatcgacgct caagtcagag gtggcgaaac ccgacaggac tataaagata ccaggcgttt   7200
ccccctggaa gctccctcgt gcgctctcct gttccgaccc tgccgcttac cggatacctg   7260
tccgcctttc tcccttcggg aagcgtggcg ctttctcata gctcacgctg taggtatctc   7320
agttcggtgt aggtcgttcg ctccaagctg ggctgtgtgc acgaaccccc cgttcagccc   7380
gaccgctgcg ccttatccgg taactatcgt cttgagtcca acccggtaag acgactta     7440 tcgccactgg cagcagccac tggtaacagg attagcagag cgaggtatgt aggcggtgct   7500
acagagttct tgaagtggtg gcctaactac ggctacacta agaacagt atttggtatc     7560 tgcgctctgc tgaagccagt taccttcgga aaaagagttg gtagctcttg atccggcaaa   7620
caaaccaccg ctggtagcgg tggttttttt gtttgcaagc agcagattac gcgcagaaaa   7680
aaaggatctc aagaagatcc tttgatcttt tctacggggt ctgacgctca gtg          7733
```

<210> SEQ ID NO 9
<211> LENGTH: 7734
<212> TYPE: DNA
<213> ORGANISM: Artificial Sequence
<220> FEATURE:
<223> OTHER INFORMATION: Allele-replacement vector for pTi plasmid Tn904
      copy

<400> SEQUENCE: 9

```
gcaggctgtg cagatcgata tggtctttcg agatgtccgc gccgatggta atatccgtca    60
tcttttctca tctcccatgc ttgtcatccg agccttaaaa ctcgggtatc cgttcaggac   120
gattggaaaa gatggggcg atcaaactct agttcggccc ggcattcgtc agaatgcgg    180 cctcgcattt cacgacccgt cccccatcgc cggaagagga tggccgtcct ctccggcgct   240
tctttatctc acgaagaagc aagaagttta taagacaagc agatcctgtt caatccgggt   300
catagcctgc agccctgaag taatttgcgc attcctccga tgtgaatcgg gggatcaatg   360
tgccgacgac atcccatagg gcgtcgatct ttcgctccgc ccgagcccgt agcatagctt   420
tcaatttcga gaatgcgttt tcgatgggat taaagtcggg actataggg ggcaggaaca    480 tgagtttgag tttgagctgt cagactgggc ttaagagccc accgagcaat gcatgagaca   540
```

```
taaagtgttg atttccatgt ggaactgagc cggttttcc tccgggaagt gagccacctc    600
tgactatggt tttatgattg gattttggtc aagggattgg cttttctcc tctcttgttt    660 gctgcggctg ccgaactggc tttgaagcgg aagctgtcat tacctgtttc caggatatgg   720
cagggatggg tcaaaggatc gagcaaatgc cgtcgtcatc ttggcgtcgc cgaagaccgt   780
tgcccattcg ctgaagctga ggttggtggt gatgatgacg ctggtgcgct cataaagctt   840
gctcagcagg tggaagagca tcgctccgcc tgaggcactg aatggaaggt atccgagctc   900
atcgaggatc agcagatcga ggcgaaccag cgtctcagcg atctggcctg ccttgccttt   960
agccttctcc tgctcgagcg cgttgaccag ttcgatggtc gagaagaagc ggaccttgcg   1020
gcgatgatgc tcgatcgcct ggacaccgag ggcggtcgcg acatgtgttt tcctgtgcc    1080 cggtccgccg acaagcacta tattctgcgc cccgtcgatg aactcgcatc tgtgcaattg   1140
gcgcaccgtc gcttcgttga tttcgctggc ggcgaagtcg tatccggaga tgtccttgta   1200
ggccgggaag cgggcagcct tcatgtgata ggcgatggac cggacctcac gctcggccat   1260
ctcggctttc agcaactggg acaggatcgg cacggccgcg tcaaaagccg gagcaccttg   1320
ctcgatcagg tccgtgacgg cttgagacat gccatacatc ttcaggctac gcagcatgat   1380
gacgacggcg gcgctggcgg gatcatgacg cattgcgacc tcccacgatc cggacacgca   1440
ggccatcgta acgttcgaca ttggccttgg gctcccgcag caaggtcagt gcctgtggcg   1500
tatcgatgtc gggaccgtct gtcgtcttgc catcaatcag catatgcaac agattcagca   1560
catgcgtttt ggttgctacg ccttgatcca gagccagttc cacagctcta acgacgacct   1620
gttcgtcgtg atggaggacg agagcgagga tatcggccat ctcgcgatca ccgccagggc   1680
ggcgcagcat ctggtcctgc agtcgtcgaa aggccagcgg caattccagg aaaggtgcgc   1740
cattgcgcag ggctccgggt ttgcgctgga tgacggcaag gtaatgccgc cagtcataga   1800
ttgtccgggg tagcctgtgg ctgcgctcga tgacccgcgc gtgttcacat agaatgtttc   1860
cctcggctgc gacgaccagg cgctcgggat atatccgcag gctgacgggc cggtttgcaa   1920
atgatgcagg cacgctgtag cggttccgct cgaaggtaat caggcatgtt ggtgagacgc   1980
gcttgctctg ctcgacgaag ccccttacg gtgggattca gagcttacgt tggttttgg    2040 ttccattgct ccccaaaccc catatgggcg ttgtcgcgga gatcgctgat cgggttcttg   2100
tgatgcgcgg gggccaggtg gtcgagtccg gtccagtgga tagcgtgttc acgcgtcctg   2160 aaagcccta cacgaaggta cttatcgagg ctgccccgtc ggttgccggg aaactggcaa    2220
cgacgggaca gcccacgacc gcaatcgatg cgctgccgct gtcctttgag ggtgaacggc   2280
caattctcga ggtccgcgat cttactgtcc gcttcccgct tcgcggaggt ctccttggaa   2340
acgttcaggg caacgttcac gccgtggaga aagcctcctt tgctatagga aagggcgaaa   2400
ctctgggact tgtcggggag tccggctcag gtaagtcaac catcggcaaa gctatcatcg   2460
atcttgcgcc gcgcttcggc ggctccattg tcgtggacgg gcgcacgatc gactacgccg   2520
acgaaaagag ccttgctgtg ttgcgccgcg atgttcagat gatcttccag gatcctttcg   2580
gttctctgga cagccgtcag acaataggat cggccattgt cgagcccatg tacgttcatg   2640
gcatcgcgtc gggccgcgag ttgcgtgaaa agatggagtg gttgctagaa aaagtcgggc   2700
ttgatccggc tcgggctagc agcctgccgc acgaattctc cggcggccag cggcaaagga   2760
tttgcattgc gcgggcactg tctatgtcgc ccaagctcat cattgccgac gaggcagtat   2820
ccgcacttga tgtagcgatc aaaggccaga tcatcgagct gatgatggac ctgcagtccg   2880
agttcggtgt gtcctaccct tcatcagcc acgacatggc cgctgtggag aagatctgca    2940
```

```
ccagggtggc cgttatgtac ttcggcgaac tggtcgagat aggtggccgc gacaatgtta    3000
tcgggcgccc gggacacagc tacaccaaac gtcttctctc ggcggtcccg atcacacatc    3060
cgagccagcg atcggcacgt tcgaccgcgg ctttgcaggt gccgcaaccg gtgagcccga    3120
ttaagccggt cgggttcatt ccgccgacgc aaaactgggc ggcgatgaac gacaagcatt    3180
tcgtgcgtgt ttgacggcct gccgcgtgcc ggagggctac gcgagccaat cgttcagcat    3240
cactcgacgg aaattgccga ggatggtcca gaggcagtga gactaatatc agtgaaaagg    3300
ggagttcgca tgagacatag agcatactgg acaagcgctg ccattgtggc cggagtgtta    3360
agcacagccg tttcgatccc aagccaggca ttcgctgcaa agaccgaact atctatgggt    3420
gttgcctctg aggatgtgac aacactcgat ccgcatttcg cgacaacgac atcagaccga    3480
acgctggttt catacatcta tggagcccct gtccgcttcg ctccgggatc ggcaaatcca    3540
tcgtccattg aagcagatct ggctgagagc tgggaatcca atgccgatca actggtgtgg    3600
accttcaagc tgcgcccaga cgtgaaatgg cagggcggat acggcaacgt gacggcagac    3660
gacgtcgtgt tcagtctgga taaggcgcgc gatccaaagc gttccgcatt ctctggcgac    3720
tatgcagcga tccagaaagt cgaggcagtt gacgcaaaga cggttcgcat tacccttaca    3780
cgacgcgtgc cgagccttct ggcgctgctt tcgaattttt ccggtggctt cattattccg    3840
aagaaggcgt tcaaagagcg cggcgatgat ttcaaacgcc ggcccgtagg ctttggccct    3900
ttccaggttg agtctattca gcctggtcaa tctgtaacgc tcacggcgaa tgccgaatac    3960
ttcaggggca agccgaaact ttcgaagatc agttacaggg gccgcggatc gatccttttt    4020
aacccatcac atatacctgc cgttcactat tatttagtga aatgagatat tatgatattt    4080
tctgaattgt gattaaaaag gcaactttat gcccatgcaa cagaaactat aaaaaataca    4140
gagaatgaaa agaaacagat agattttta gttctttagg cccgtagtct gcaaatcctt    4200
ttatgatttt ctatcaaaca aaagaggaaa atagaccagt tgcaatccaa acgagagtct    4260
aatagaatga ggtcgaaaag taaatcgcgc gggtttgtta ctgataaagc aggcaagacc    4320
taaaatgtgt aaagggcaaa gtgtatactt tggcgtcacc ccttacatat tttaggtctt    4380
tttttattgt gcgtaactaa cttgccatct tcaaacagga gggctggaag aagcagaccg    4440
ctaacacagt ataaaaaaa ggagacatga acgatgaaca tcaaaaagtt tgcaaaacaa    4500
gcaacagtat taacctttac taccgcactg ctggcaggag gcgcaactca agcgtttgcg    4560
aaagaaacga accaaaagcc atataaggaa acatacggca tttcccatat tacacgccat    4620
gatatgctgc aaatccctga acagcaaaaa atgaaaaat atcaagttcc tgaattcgat    4680
tcgtccacaa ttaaaaatat ctcttctgca aaaggcctgg acgtttggga cagctggcca    4740
ttacaaaacg ctgacggcac tgtcgcaaac tatcacggct accacatcgt ctttgcatta    4800
gccggagatc ctaaaaatgc ggatgacaca tcgatttaca tgttctatca aaaagtcggc    4860
gaaacttcta ttgacagctg gaaaaacgct ggcgcgtct ttaaagacag cgacaaattc    4920
gatgcaaatg attctatcct aaaagaccaa acacaagaat ggtcaggttc agccacattt    4980
acatctgacg gaaaaatccg tttattctac actgatttct ccggtaaaca ttacggcaaa    5040
caaacactga caactgcaca gttaacgta tcagcatcag acagctcttt gaacatcaac    5100
ggtgtagagg attataaatc aatctttgac ggtgacggaa aaacgtatca aaatgtacag    5160
cagttcatcg atgaaggcaa ctacagctca ggcgacaacc atacgctgag agatcctcac    5220
tacgtagaag ataaaggcca caaatactta gtatttgaag caaacactgg aactgaagat    5280
```

```
ggctaccaag gcgaagaatc tttatttaac aaagcatact atggcaaaag cacatcattc    5340
ttccgtcaag aaagtcaaaa acttctgcaa agcgataaaa aacgcacggc tgagttagca    5400
aacggcgctc tcggtatgat tgagctaaac gatgattaca cactgaaaaa agtgatgaaa    5460
ccgctgattg catctaacac agtaacagat gaaattgaac gcgcgaacgt ctttaaaatg    5520
aacggcaaat ggtacctgtt cactgactcc cgcggatcaa aaatgacgat tgacggcatt    5580
acgtctaacg atatttacat gcttggttat gtttctaatt ctttaactgg cccatacaag    5640
ccgctgaaca aaactggcct tgtgttaaaa atggatcttg atcctaacga tgtaaccttt    5700
acttactcac acttcgctgt acctcaagcg aaaggaaaca atgtcgtgat tacaagctat    5760
atgacaaaca gaggattcta cgcagacaaa caatcaacgt tgcgccaagc ttcctgctg    5820 aacatcaaag gcaagaaaac atctgttgtc aaagacagca tccttgaaca aggcaattaa   5880
acagttaaca aataaggccg gcctcgcgaa tgcatctaga tccaatccaa tatgcatggc    5940
atgccgaatc catgtgggag tttattcttg acacagatat ttatgatata ataactgagt    6000
aagcttaaca taaggaggaa aaacatatgt tacgcagcag caacgatgtt acgcagcagg    6060
gcagtcgccc taaaacaaag ttaggtggct caagtatggg catcattcgc acatgtaggc    6120
tcggccctga ccaagtcaaa tccatgcggg ctgctcttga tcttttcggt cgtgagttcg    6180
gagacgtagc cacctactcc caacatcagc cggactccga ttacctcggg aacttgctcc    6240
gtagtaagac attcatcgcg cttgctgcct tcgaccaaga agcggttgtt ggcgctctcg    6300
cggcttacgt tctgcccaag tttgagcagc gcgtagtga gatctatatc tatgatctcg     6360
cagtctccgg cgagcaccgg aggcagggca ttgccaccgc gctcatcaat ctcctcaagc    6420
atgaggccaa cgcgcttggt gcttatgtga tctacgtgca agcagattac ggtgacgatc    6480
ccgcagtggc tctctataca aagttgggca tacgggaaga agtgatgcac tttgatatcg    6540
acccaagtac cgccacctaa taatgtctaa caattcgttc aagccgacgc cgcttcgcgg    6600
cgcggcttaa ctcaagcgtt agatgcacta tacgtaccaa tccaaatcgg atcccgggcc    6660
cgtcgactgc agaggcctgc atgcaagctt ggcgtaatca tggtcatagc tgtttcctgt    6720
gtgaaattgt tatccgctca caattccaca acatacga gccggaagca taaagtgtaa     6780
agcctggggt gcctaatgag tgagctaact cacattaatt gcgttgcgct cactgcccgc    6840
tttccagtcg ggaaacctgt cgtgccagct gcattaatga atcggccaac gcgcggggag    6900
aggcggtttg cgtattgggc gctcttccgc ttcctcgctc actgactcgc tgcgctcggt    6960
cgttcggctg cggcgagcgg tatcagctca ctcaaaggcg gtaatacggt tatccacaga    7020
atcaggggat aacgcaggaa agaacatgtg agcaaaaggc cagcaaaagg ccaggaaccg    7080
taaaaaggcc gcgttgctgg cgttttttcca taggctccgc ccccctgacg agcatcacaa    7140
aaatcgacgc tcaagtcaga ggtggcgaaa cccgacagga ctataaagat accaggcgtt    7200
tccccctgga agctccctcg tgcgctctcc tgttccgacc ctgccgctta ccggatacct    7260
gtccgccttt ctcccttcgg gaagcgtggc gctttctcat agctcacgct gtaggtatct    7320
cagttcggtg taggtcgttc gctccaagct gggctgtgtg cacgaacccc ccgttcagcc    7380
cgaccgctgc gccttatccg gtaactatcg tcttgagtcc aacccggtaa gacacgactt    7440
atcgccactg gcagcagcca ctggtaacag gattagcaga gcgaggtatg taggcggtgc    7500
tacagagttc ttgaagtggt ggcctaacta cggctacact agaagaacag tatttggtat    7560
```

```
ctgcgctctg ctgaagccag ttaccttcgg aaaaagagtt ggtagctctt gatccggcaa    7620
acaaaccacc gctggtagcg gtggtttttt tgtttgcaag cagcagatta cgcgcagaaa    7680
aaaaggatct caagaagatc ctttgatctt ttctacgggg tctgacgctc agtg          7734
```

MODIFIED *AGROBACTERIUM* STRAINS AND USE THEREOF FOR PLANT TRANSFORMATION

FIELD OF THE DISCLOSURE

The present disclosure relates generally to the field of plant molecular biology, including genetic manipulation of plants. More specifically, the present disclosure pertains to modified *Agrobacterium* strains, methods of making such modified *Agrobacterium* strains, as well as, methods of using such modified *Agrobacterium* strains for producing a transformed plant and transformed plants so produced.

CROSS-REFERENCE TO RELATED APPLICATIONS

This application claims the benefit of PCT Application Serial Number PCT/US2020/024993, filed Mar. 26, 2020, which claims the benefit of U.S. Provisional Patent Application No. 62/825,054 filed on Mar. 28, 2019, all of which are hereby incorporated herein in their entireties by reference.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 7777-US-PCT ST25, created on Jul. 14, 2021, and having a size of 38,150 bytes and is filed concurrently with the specification. The sequence listing contained in this ASCII formatted document is part of the specification and is herein incorporated by reference in its entirety.

BACKGROUND

The *Agrobacterium tumefaciens* (*Agrobacterium radiobacter, Rhizobiuum radiobacter*) strain LBA4404 ("LBA4404") is commonly used for integrating a T-strand within the genome of a plant cell. The *Agrobacterium tumefaciens* LBA4404 strain has been modified to produce a thymidine auxotroph *Agrobacterium tumefaciens* LBA4404 THY– ("LBA4404 THY–"), which is also used for integrating a T-strand within the genome of a plant cell. LBA4404 and LBA4404 THY– each contain two (2) copies of the Tn904 transposon. The Tn904 transposon (Tn904) is active in LBA4404 and LBA4404 THY– and can insert a copy of itself into the chromosome, a T-DNA vector, a resident Ti plasmid, or a vir gene helper plasmid. These insertions undesirably impact the quality and efficiency of vector quality control processes. The insertion of a copy of the Tn904 transposon into a T-DNA and subsequently into a plant chromosome has been detected in rice and maize transformed with LBA4404. These insertions undesirably impact the quality and efficiency of plant transformation processes. Insertion of Tn904 into transgenic events may increase the time and expense of obtaining regulatory approval of such transgenic events. Tn904 has two aminoglycoside O-phosphotransferase genes conferring resistance to streptomycin and a heavy metal efflux pump conferring mercury resistance.

Thus, there remains a need for improved strains of *Agrobacterium tumefaciens* without highly active transposons that may lead to the spread of antibiotic resistance genes. In particular, development of strains of *Agrobacterium tumefaciens* lacking the Tn904 transposon would be desirable.

SUMMARY

The present disclosure comprises modified *Agrobacterium* compositions, methods of making such modified *Agrobacterium* compositions, as well as, methods of using such compositions modified *Agrobacterium* for producing a transgenic plant.

In an aspect, the disclosure provides a genetically modified *Agrobacterium tumefaciens* bacterium, wherein a functional Tn904 transposon is not present. In an aspect, the modified *Agrobacterium tumefaciens* bacterium is *A. tumefaciens* LBA4404 or *A. tumefaciens* LBA4404 THY–. In an aspect, the *Agrobacterium tumefaciens* bacterium demonstrates sensitivity to streptomycin due to the non-functional Tn904 transposon. In an aspect, the Tn904 transposon is removed or rendered non-functional by allele replacement. In an aspect, the Tn904 transposon comprises a sequence that is at least 95% identical to SEQ ID NO: 7. In an aspect, the modified *Agrobacterium tumefaciens* bacterium further comprises a binary plasmid comprising a T-DNA having a polynucleotide of interest encoding a polypeptide that confers a trait to a plant. In an aspect, the trait confers a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing. In an aspect, the modified *Agrobacterium tumefaciens* bacterium is a modified *A. tumefaciens* LBA4404 strain. In an aspect, the modified *Agrobacterium tumefaciens* bacterium is a modified *A. tumefaciens* LBA4404. THY– strain. In an aspect, the modified *Agrobacterium tumefaciens* bacterium further comprises a disarmed Ti plasmid. In an aspect, the modified *Agrobacterium tumefaciens* bacterium further comprises a binary plasmid comprising a T-DNA with a polynucleotide of interest encoding a polypeptide that confers a trait to a plant. In an aspect, the trait confers a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing. In an aspect, the disarmed Ti plasmid is pVIR9. In an aspect, the modified *Agrobacterium tumefaciens* bacterium is derived from *Agrobacterium tumefaciens* LBA4404. In an aspect, the modified *Agrobacterium tumefaciens* bacterium is derived from *Agrobacterium tumefaciens* LBA4404 THY–.

In an aspect, the present disclosure provides a method of transforming a plant, comprising: contacting a plant cell with the modified *Agrobacterium tumefaciens* bacterium under conditions that permit the modified *Agrobacterium tumefaciens* bacterium to infect the plant cell, thereby transforming the plant cell; selecting and screening the transformed plant cells; and regenerating whole transgenic plants from the selected and screened plant cells. In an aspect, the transgenic plants comprise a polynucleotide of interest encoding a polypeptide that confers a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing. In an aspect, the plant cell is a barley cell, a maize cell, a millet cell, an oat cell, a rice cell, a rye cell, a *Setaria* sp. cell, a sorghum cell, a sugarcane cell, a switchgrass cell, a triticale cell, a turfgrass cell, a wheat cell, a kale cell, a cauliflower cell, a broccoli cell, a mustard plant cell, a cabbage cell, a pea cell, a clover cell, an alfalfa cell, abroad bean cell, a tomato cell, a cassava cell, a soybean cell, a canola cell, a sunflower cell, a safflower cell, a tobacco cell, an *Arabidopsis* cell, or a cotton cell.

In an aspect, the present disclosure provides a modified *Agrobacterium tumefaciens* strain that is deficient in a functional Tn904 transposon relative to its parent strain. In an aspect, the Tn904 transposon comprises a sequence that is at least 95% identical to SEQ ID NO: 7. In an aspect, the modified *Agrobacterium tumefaciens* strain further comprises a disarmed Ti plasmid. In an aspect, the disarmed Ti plasmid is a pVIR9 plasmid. In an aspect, the parent strain is *Agrobacterium tumefaciens* LBA4404. In an aspect, the parent strain is *Agrobacterium tumefaciens* LBA4404 THY−.

In an aspect, the methods of the disclosure provide a transgenic plant event comprising: a plant cell comprising a T-strand insert flanked by (a) an upstream genomic DNA border sequence; and (b) a downstream genomic DNA border sequence, wherein the plant cell used to regenerate the transgenic plant event comprises integration of the T-strand from a modified strain of *Agrobacterium tumefaciens*, wherein the modified strain of *Agrobacterium tumefaciens* does not comprise a Tn904 transposon or is deficient in a functional Tn904 transposon relative to its parent strain. In an aspect, the T-strand insert comprises a polynucleotide of interest encoding a polypeptide that confers a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing. In an aspect, the plant cell is a barley cell, a maize cell, a millet cell, an oat cell, a rice cell, a rye cell, a *Setaria* sp. cell, a sorghum cell, a sugarcane cell, a switchgrass cell, a triticale cell, a turfgrass cell, a wheat cell, a kale cell, a cauliflower cell, a broccoli cell, a mustard plant cell, a cabbage cell, a pea cell, a clover cell, an alfalfa cell, a broad bean cell, a tomato cell, a cassava cell, a soybean cell, a canola cell, a sunflower cell, a safflower cell, a tobacco cell, an *Arabidopsis* cell, or a cotton cell.

In an aspect, the present disclosure provides a method of producing a transgenic plant, comprising: (a) contacting a plant cell with a modified *Agrobacterium tumefaciens* strain, which is deficient in a functional Tn904 transposon relative to its parent strain; (b) selecting and screening plant cells comprising a T-DNA from the modified *Agrobacterium tumefaciens* strain integrated into the genome of the plant cell; and (c) regenerating a whole transgenic plant from the plant cell selected and screened in step (b). In an aspect, the T-DNA from the modified *Agrobacterium tumefaciens* strain integrated into the genome of the plant cells comprises a polynucleotide of interest encoding a polypeptide that confers a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing. In an aspect, the plant cell is a barley cell, a maize cell, a millet cell, an oat cell, a rice cell, a rye cell, a *Setaria* sp. cell, a sorghum cell, a sugarcane cell, a switchgrass cell, a triticale cell, a turfgrass cell, a wheat cell, a kale cell, a cauliflower cell, a broccoli cell, a mustard plant cell, a cabbage cell, a pea cell, a clover cell, an alfalfa cell, abroad bean cell, a tomato cell, a cassava cell, a soybean cell, a canola cell, a sunflower cell, a safflower cell, a tobacco cell, an *Arabidopsis* cell, or a cotton cell.

In an aspect, the present disclosure provides a modified strain of *Agrobacterium tumefaciens*, wherein the modified strain is *A. tumefaciens* LBA4404 THY− strain deposited with the ATCC, assigned Accession Number PTA-10531 wherein a functional Tn904 transposon is not present or a Tn904 transposon has been deleted. In an aspect, the deletion of the Tn904 transposon comprises SEQ ID NO: 7. In an aspect, the modified *Agrobacterium tumefaciens* strain further comprises a disarmed Ti plasmid. In an aspect, the disarmed Ti plasmid is a pVIR9 plasmid.

In an aspect, the present disclosure provides a method of producing a transgenic plant, comprising: (a) contacting a plant cell with the modified *Agrobacterium tumefaciens* strain, wherein the modified *Agrobacterium tumefaciens* strain is deficient in a functional Tn904 transposon relative to its parent strain; (b) selecting and screening a plant cell comprising DNA from said *Agrobacterium* strain integrated into the genome of the plant cell; and (c) regenerating a whole transgenic plant from the plant cell selected and screened in step (b). In an aspect, the DNA from the modified *Agrobacterium tumefaciens* strain integrated into the genome of the plant cell comprises a polynucleotide of interest encoding a polypeptide that confers a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing. In an aspect, the plant cell is a barley cell, a maize cell, a millet cell, an oat cell, a rice cell, a rye cell, a *Setaria* sp. cell, a sorghum cell, a sugarcane cell, a switchgrass cell, a triticale cell, a turfgrass cell, a wheat cell, a kale cell, a cauliflower cell, a broccoli cell, a mustard plant cell, a cabbage cell, a pea cell, a clover cell, an alfalfa cell, abroad bean cell, a tomato cell, a cassava cell, a soybean cell, a canola cell, a sunflower cell, a safflower cell, a tobacco cell, an *Arabidopsis* cell, or a cotton cell. In an aspect, DNA from the modified *Agrobacterium tumefaciens* strain comprises a binary vector comprising a T-DNA for transformation of plants. In an aspect, the modified *Agrobacterium tumefaciens* strain further comprises a pVIR9 plasmid. In an aspect, the T-DNA comprises a gene encoding a polypeptide that confers a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing.

In an aspect, the present disclosure provides a streptomycin sensitive, genetically modified *Agrobacterium tumefaciens* strain for transforming a plant cell.

In an aspect, the present disclosure provides a method of genetically modifying a streptomycin resistant *Agrobacterium tumefaciens* strain to streptomycin sensitive, the method comprising modifying a transposon encoding a streptomycin kinase. In an aspect, the modification comprises allele replacement of Tn904. In an aspect, the modification comprises a mutation in the coding region of Tn904 encoding the streptomycin kinase. In an aspect, the modification comprises deletion of the transposon Tn904.

BRIEF DESCRIPTION OF THE FIGURE

FIG. 1, further described in Example 2, shows a diagrammatic illustration of the generation of the Tn904− strain. A plasmid containing a Tn904-deleted allele with kb of flanking DNA of each side was cloned into a plasmid able to replicate in *E. coli*, but not *Agrobacterium*. Transformation of this plasmid into *Agrobacterium* with gentamicin selection resulted in the plasmid integrating into the chromosome at a cloned region of homology. Integration can occur by recombination on either side of the plasmid allele of interest (A or B). A second recombination event between the newly created direct repeats will lead to plasmid excision. For excision to lead to a successful allelic exchange, recombination must occur in the second region of homology. PCR screening primer positions are shown with arrows (→ or ←).

DETAILED DESCRIPTION

The disclosures herein will be described more fully hereinafter with reference to the accompanying FIGURE, in which some, but not all possible aspects are shown. Indeed, disclosures may be embodied in many different forms and should not be construed as limited to the aspects set forth herein; rather, these aspects are provided so that this disclosure will satisfy applicable legal requirements.

Many modifications and other aspects disclosed herein will come to mind to one skilled in the art to which the disclosed compositions, methods of making such compositions, as well as, methods of using such compositions for producing a transformed plant and transformed plants so produced, pertain having the benefit of the teachings presented in the following descriptions and the associated FIGURE. Therefore, it is to be understood that the disclosures are not to be limited to the specific aspects disclosed and that modifications and other aspects are intended to be included within the scope of the appended claims. Although specific terms are employed herein, they are used in a generic and descriptive sense only and not for purposes of limitation.

The terminology used herein is for the purpose of describing particular aspects only and is not intended to be limiting. As used in the specification and in the claims, the term "comprising" can include the aspect of "consisting of". Unless defined otherwise, all technical and scientific terms used herein have the same meaning as commonly understood by one of ordinary skill in the art to which the disclosed compositions and methods of using such compositions belong. In this specification and in the claims which follow, reference will be made to a number of terms which shall be defined herein.

In an aspect, the present disclosure comprises compositions, methods of making such compositions, as well as, methods of using such compositions for producing a transgenic plant. The term "plant" refers to whole plants, plant organs (e.g., leaves, stems, roots, etc.), plant tissues, plant cells, plant parts, seeds, propagules, embryos and progeny of the same. Plant cells can be differentiated or undifferentiated (e.g. callus, undifferentiated callus, immature and mature embryos, immature zygotic embryo, immature cotyledon, embryonic axis, suspension culture cells, protoplasts, leaf, leaf cells, root cells, phloem cells and pollen). Plant cells include, without limitation, cells from seeds, suspension cultures, explants, immature embryos, embryos, zygotic embryos, somatic embryos, embryogenic callus, meristem, somatic meristems, organogenic callus, protoplasts, embryos derived from mature ear-derived seed, leaf bases, leaves from mature plants, leaf tips, immature inflorescences, tassel, immature ear, silks, cotyledons, immature cotyledons, embryonic axes, meristematic regions, callus tissue, cells from leaves, cells from stems, cells from roots, cells from shoots, gametophytes, sporophytes, pollen and microspores. Plant parts include differentiated and undifferentiated tissues including, but not limited to, roots, stems, shoots, leaves, pollen, seeds, tumor tissue and various forms of cells in culture (e. g., single cells, protoplasts, embryos, and callus tissue). The plant tissue may be in a plant or in a plant organ, tissue, or cell culture. Grain is intended to mean the mature seed produced by commercial growers for purposes other than growing or reproducing the species. Progeny, variants and mutants of the regenerated plants are also included within the scope of the disclosure, provided these progeny, variants and mutants comprise the introduced polynucleotides.

The present disclosure may be used for transformation of any plant species, including, but not limited to, monocots and dicots. Monocots include, but are not limited to, barley, maize (corn), millet (e.g., pearl millet (*Pennisetum glaucum*), proso millet (*Panicum miliaceum*), foxtail millet (*Setaria Italica*), finger millet (*Eleusine coracana*), teff (*Eragrostis tef*), oats, rice, rye, *Setaria* sp., sorghum, triticale, or wheat, or leaf and stem crops, including, but not limited to, bamboo, marram grass, meadow-grass, reeds, ryegrass, sugarcane; lawn grasses, ornamental grasses, and other grasses such as switchgrass and turf grass. Alternatively, dicot plants used in the present disclosure, include, but are not limited to, kale, cauliflower, broccoli, mustard plant, cabbage, pea, clover, alfalfa, broad bean, tomato, peanut, cassava, soybean, canola, alfalfa, sunflower, safflower, tobacco, *Arabidopsis*, or cotton.

Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria Italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygd-*

*alus*), sugar beets (*Beta vulgaris*), sugarcane (*Saccharum* spp.), oats, barley, vegetables, ornamentals, and conifers.

Higher plants, e.g., classes of Angiospermae and Gymnospermae may be used the present disclosure. Plants of suitable species useful in the present disclosure may come from the family Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, and Vitaceae. Plants from members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Mus*a, *Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea mays* be used in the methods of the disclosure, using the modified *Agrobacterium* strains disclosed herein.

Plants important or interesting for agriculture, horticulture, biomass production (for production of liquid fuel molecules and other chemicals), and/or forestry may be used in the methods of the disclosure, using the modified *Agrobacterium* strains disclosed herein. Non-limiting examples include, for instance, *Panicum virgatum* (switchgrass), *Miscanthus giganteus* (miscanthus), *Saccharum* spp. (sugarcane, energycane), *Populus* balsamifera (poplar), cotton (*Gossypium barbadense, Gossypium hirsutum*), *Helianthus annuus* (sunflower), *Medicago sativa* (alfalfa), *Beta vulgaris* (sugarbeet), sorghum (*Sorghum bicolor, Sorghum vulgare*), *Erianthus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Arundo donax* (giant reed), *Secale cereale* (rye), *Salix* spp. (willow), *Eucalyptus* spp. (eucalyptus, including *E. grandis* (and its hybrids, known as "urograndis"), *E. globulus, E. camaldulensis, E. tereticornis, E. viminalis, E. nitens, E. saligna* and *E. urophylla*), Triticosecale spp. (*triticum*—wheat X rye), teff (*Eragrostis tef*), Bamboo, *Carthamus tinctorius* (safflower), *Jatropha curcas* (jatropha), *Ricinus communis* (castor), *Elaeis guineensis* (palm), *Linum usitatissimum* (flax), *Manihot esculenta* (cassava), *Lycopersicon esculentum* (tomato), *Lactuca sativa* (lettuce), *Phaseolus vulgaris* (green beans), *Phaseolus limensis* (lima beans), *Lathyrus* spp. (peas), *Musa paradisiaca* (banana), *Solanum tuberosum* (potato), *Brassica* spp. (*B. napus* (canola), *B. rapa, B. juncea*), *Brassica oleracea* (broccoli, cauliflower, brussel sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Arachis hypogaea* (peanuts), *Ipomoea batatus* (sweet potato), *Cocos nucifera* (coconut), *Citrus* spp. (citrus trees), *Persea americana* (avocado), fig (*Ficus casica*), guava (*Psidium guajava*), mango (*Mangifera indica*), olive (*Olea europaea*), *Carica papaya* (papaya), *Anacardium occidentale* (cashew), *Macadamia integrifolia* (macadamia tree), *Prunus amygdalus* (almond), *Allium cepa* (onion), *Cucumis melo* (musk melon), *Cucumis sativus* (cucumber), *Cucumis cantalupensis* (cantaloupe), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Cyamopsis tetragonoloba* (guar bean), *Ceratonia siliqua* (locust bean), *Trigonella foenum-graecum* (fenugreek), *Vigna radiata* (mung bean), *Vigna unguiculata* (cowpea), *Vicia faba* (fava bean), *Cicer arietinum* (chickpea), *Lens culinaris* (lentil), *Papaver somniferum* (opium poppy), *Papaver orientate, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana* (achiote), *Alstroemeria* spp., *Rosa* spp. (rose), *Rhododendron* spp. (azalea), *Macrophylla hydrangea* (hydrangea), *Hibiscus rosasanensis* (hibiscus), *Tulipa* spp. (tulips), *Narcissus* spp. (daffodils), *Petunia hybrida* (petunias), *Dianthus caryophyllus* (carnation), *Euphorbia pulcherrima* (poinsettia), *chrysanthemum, Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass), *Phleum pratense* (timothy), and conifers.

Conifers may be used in the present disclosure and include, for example, pines such as loblolly pine (*Pinus taeda*), slash pine (*Pinus elliotii*), ponderosa pine (*Pinus ponderosa*), qlodgepole pine (*Pinus contorta*), and Monterey pine (*Pinus radiata*); Douglas-fir (*Pseudotsuga menziesii*); Eastern or Canadian hemlock (*Tsuga canadensis*); Western hemlock (*Tsuga heterophylla*); Mountain hemlock (*Tsuga mertensiana*); Tamarack or Larch (*Larix occidentalis*); Sitka spruce (*Picea glauca*); redwood (*Sequoia sempervirens*); true first such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turf grasses may be used in the present disclosure and include, but are not limited to: annual bluegrass (*Poa annua*); annual ryegrass (*Lolium multiflorum*); Canada bluegrass (*Poa compressa*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivi-* alis); sheep fescue (*Festuca ovina*); smooth bromegrass (*Bromus inermis*); timothy (*Phleum pratense*); velvet bentgrass (*Agrostis canina*); weeping alkaligrass (*Puccinellia distans*); western wheatgrass (*Agropyron smithii*); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

In specific aspects, plants transformed by the compositions and methods of the present disclosure, using the modified *Agrobacterium* strains disclosed herein, are crop plants (for example, corn, alfalfa, sunflower, *Brassica*, soybean, cotton, safflower, peanut, rice. sorghum, wheat, millet, tobacco, etc.). Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include, but are not limited to, beans and peas. Beans include, but are not limited to, guar, locust bean, fenugreek, soybean, garden beans, cowpea, mungbean, lima bean, fava bean, lentils, and chickpea.

In an aspect, the present disclosure also includes plants obtained by using any of the compositions disclosed herein in the methods disclosed herein, using the modified *Agrobacterium* strains disclosed herein. In an aspect, the present disclosure also includes seeds from a plant obtained by using any of the compositions disclosed herein in the methods disclosed herein, using the modified *Agrobacterium* strains disclosed herein. A transgenic plant is defined as a mature, fertile plant that contains a transgene.

In the disclosed methods, using the modified *Agrobacterium* strains disclosed herein, various plant-derived explants can be used, including immature embryos, 1-5 mm zygotic embryos, 3-5 mm embryos, and embryos derived from mature ear-derived seed, leaf bases, leaves from mature plants, leaf tips, immature inflorescences, tassel, immature ear, and silks. In an aspect, the explants used in the disclosed methods, using the modified *Agrobacterium* strains disclosed herein, can be derived from mature ear-derived seed, leaf bases, leaves from mature plants, leaf tips, immature inflorescences, tassel, immature ear, and silks. The explant used in the disclosed methods, using the modified *Agrobacterium* strains disclosed herein, can be derived from any of the plants described herein.

The disclosure encompasses isolated or substantially purified nucleic acid compositions. An "isolated" or "purified" nucleic acid molecule or protein or a biologically active portion thereof is substantially free of other cellular material or components that normally accompany or interact with the nucleic acid molecule or protein as found in its naturally occurring environment or is substantially free of culture medium when produced by recombinant techniques or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the organism from which the nucleic acid is derived. For example, in various aspects, an isolated nucleic acid molecule can contain less than about 5 kb, 4 kb, 3 kb, 2 kb, 1 kb, 0.5 kb or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When a protein useful in transformation methods, using the modified *Agrobacterium* strains of the disclosure or biologically active portion thereof is recombinantly produced, optimally culture medium represents less than about 30%, 20%, 10%, 5%, or 1% (by dry weight) of chemical precursors or non-protein-of-interest chemicals. Sequences useful in transformation methods, using the modified *Agrobacterium* strains of the disclosure may be isolated from the 5' untranslated region flanking their respective transcription initiation sites. The present disclosure encompasses isolated or substantially purified nucleic acid or protein compositions useful in transformation methods, using the modified *Agrobacterium* strains of the disclosure.

As used herein, the term "fragment" refers to a portion of the nucleic acid sequence. Fragments of sequences useful in transformation methods, using the modified *Agrobacterium* strains of the disclosure retain the biological activity of the nucleic acid sequence. Alternatively, fragments of a nucleotide sequence that are useful as hybridization probes may not necessarily retain biological activity. Fragments of a nucleotide sequence disclosed herein may range from at least about 20, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, or 1900, nucleotides, and up to the full length of the subject sequence. A biologically active portion of a nucleotide sequence can be prepared by isolating a portion of the sequence and assessing the activity of the portion.

Fragments and variants of nucleotide sequences and the proteins encoded thereby useful in transformation methods, using the modified *Agrobacterium* strains of the present disclosure are also encompassed. As used herein, the term "fragment" refers to a portion of a nucleotide sequence and hence the protein encoded thereby or a portion of an amino acid sequence. Fragments of a nucleotide sequence may encode protein fragments that retain the biological activity of the native protein. Alternatively, fragments of a nucleotide sequence useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins useful in transformation methods, using the modified *Agrobacterium* strains of the disclosure.

As used herein, the term "variants" is means sequences having substantial similarity with a sequence disclosed herein. A variant comprises a deletion and/or addition of one or more nucleotides or peptides at one or more internal sites within the native polynucleotide or polypeptide and/or a substitution of one or more nucleotides or peptides at one or more sites in the native polynucleotide or polypeptide. As used herein, a "native" nucleotide or peptide sequence comprises a naturally occurring nucleotide or peptide sequence, respectively. For nucleotide sequences, naturally occurring variants can be identified with the use of well-known molecular biology techniques, such as, for example, with polymerase chain reaction (PCR) and hybridization techniques as outlined herein. A biologically active variant of a protein useful in transformation methods, using the modified *Agrobacterium* strains of the disclosure may differ from that native protein by as few as 1-15 amino acid residues, as few as 1-10, such as 6-10, as few as 5, as few as 4, 3, 2, or even 1 amino acid residue.

Variant nucleotide sequences also include synthetically derived nucleotide sequences, such as those generated, for example, by using site-directed mutagenesis. Generally, variants of a nucleotide sequence disclosed herein will have at least 40%, 50%, 60%, 65%, 70%, 75%, 80%, 85%, 90%, 91%, 92%, 93%, 94%, to 95%, 96%, 97%, 98%, 99% or more sequence identity to that nucleotide sequence as determined by sequence alignment programs described elsewhere herein using default parameters. Biologically active variants of a nucleotide sequence disclosed herein are also encompassed. Biological activity may be measured by using techniques such as Northern blot analysis, reporter activity measurements taken from transcriptional fusions, and the like. See, for example, Sambrook, et al., (1989) Molecular Cloning: A Laboratory Manual (2d ed., Cold Spring Harbor Laboratory Press, Cold Spring Harbor, N.Y.), hereinafter "Sambrook", herein incorporated by reference in its entirety. Alternatively, levels of a reporter gene such as green fluorescent protein (GFP) or yellow fluorescent protein (YFP) or the like produced under the control of a promoter operably linked to a nucleotide fragment or variant can be measured. See, for example, Matz et al. (1999) Nature Biotechnology 17:969-973; U.S. Pat. No. 6,072,050, herein incorporated by reference in its entirety; Nagai, et al., (2002) Nature Biotechnology 20(1):87-90. Variant nucleotide sequences also encompass sequences derived from a mutagenic and recombinogenic procedure such as DNA shuffling. With such a procedure, one or more different nucleotide sequences can be manipulated to create a new nucleotide sequence. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, (1994) Proc. Natl. Acad. Sci. USA 91:10747-10751; Stemmer, (1994) Nature 370:389 391; Crameri, et al., (1997) Nature Biotech. 15:436-438; Moore, et al., (1997) J. Mol. Biol. 272:336-347; Zhang, et al., (1997) Proc. Natl. Acad. Sci. USA 94:4504-4509; Crameri, et al., (1998) Nature 391:288-291 and U.S. Pat. Nos. 5,605,793 and 5,837,458, herein incorporated by reference in their entirety.

Methods for mutagenesis and nucleotide sequence alterations are well known in the art. See, for example, Kunkel, (1985) Proc. Natl. Acad. Sci. USA 82:488-492; Kunkel, et al., (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein, herein incorporated by reference in their entirety. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

The nucleotide sequences of the disclosure can be used to isolate corresponding sequences from other organisms, particularly other plants, more particularly other monocots or dicots. In this manner, methods such as PCR, hybridization and the like can be used to identify such sequences based on their sequence homology to the sequences set forth herein. Sequences isolated based on their sequence identity to the entire sequences set forth herein or to fragments thereof are encompassed by the present disclosure.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in, Sambrook, supra. See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York), herein incorporated by reference in their entirety. Known methods of PCR include, but are not limited to, methods using paired primers, nested primers, single specific primers, degenerate primers, gene-specific primers, vector-specific primers, partially-mismatched primers and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides and may be labeled with a detectable group such as 32P or any other detectable marker. Thus, for example, probes for hybridization can be made by labeling synthetic oligonucleotides based on the sequences of the disclosure. Methods for preparation of probes for hybridization and for construction of genomic libraries are generally known in the art and are disclosed in Sambrook, supra.

In general, sequences that have activity and hybridize to the sequences disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 85%, 90%, 95% to 98% sequence similarity.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) CABIOS 4:11-17; the algorithm of Smith, et al., (1981) Adv. Appl. Math. 2:482; the algorithm of Needleman and Wunsch, (1970) J. Mol. Biol. 48:443-453; the algorithm of Pearson and Lipman, (1988) Proc. Natl. Acad. Sci. 85:2444-2448; the algorithm of Karlin and Altschul, (1990) Proc. Natl. Acad. Sci. USA 872:264, modified as in Karlin and Altschul, (1993) Proc. Natl. Acad. Sci. USA 90:5873-5877, herein incorporated by reference in their entirety. Computer implementations of these mathematical algorithms are well known in the art and can be utilized for comparison of sequences to determine sequence identity.

As used herein, "sequence identity" or "identity" in the context of two nucleic acid or polypeptide sequences refers to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically, this involves scoring a conservative substitution as a partial rather than a full mismatch, thereby increasing the percentage sequence identity. Thus, for example, where an identical amino acid is given a score of one and a non-conservative substitution is given a score of zero, a conservative substitution is given a score between zero and one. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, optimally at least 80%, more optimally at least 90% and most optimally at least 95%, compared to a reference sequence using an alignment program using standard parameters. One of skill in the art will recognize that these values can be appropriately adjusted to determine corresponding identity of proteins encoded by two nucleotide sequences by considering codon degeneracy, amino acid similarity, reading frame positioning and the like. Substantial identity of amino acid sequences for these purposes normally means sequence identity of at least 60%, 70%, 80%, 90% and at least 95%.

Another indication that nucleotide sequences are substantially identical is if two molecules hybridize to each other under stringent conditions. Generally, stringent conditions are selected to be about 5° C. lower than the Tm for the specific sequence at a defined ionic strength and pH. However, stringent conditions encompass temperatures in the range of about 1° C. to about 20° C. lower than the Tm, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

"Variants" is intended to mean substantially similar sequences. For polynucleotides, conservative variants include those sequences that, because of the degeneracy of the genetic code, encode the amino acid sequence of one of the morphogenic genes and/or genes/polynucleotides of interest disclosed herein. Variant polynucleotides also include synthetically derived polynucleotides, such as those generated, for example, by using site-directed mutagenesis but which still encode a protein of a morphogenic gene and/or gene/polynucleotide of interest disclosed herein. Generally, variants of a particular morphogenic gene and/or gene/polynucleotide of interest disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular morphogenic gene and/or gene/polynucleotide of interest as determined by sequence alignment programs and parameters described elsewhere herein.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present disclosure are biologically active, that is they continue to possess the desired biological activity of the native protein, that is, the polypeptide has morphogenic gene and/or gene/polynucleotide of interest activity. Such variants may result from, for example, genetic polymorphism or from human manipulation. Biologically active variants of a native morphogenic gene and/or gene/polynucleotide of interest protein disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the disclosure may differ from that protein by as few as 1-15 amino acid residues, as few as 1-10, such as 6-10, as few as 5, as few as 4, 3, 2, or even 1 amino acid residue.

The modified *Agrobacterium* strains disclosed herein are useful for the genetic engineering of plants, e.g. to produce a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part or plant the genotype of which has been altered by the presence of a heterologous nucleic acid including those transgenics initially so altered as well as those created by sexual crosses or asexual propagation from the initial transgenic.

A transgenic "event" is produced by transformation of plant cells with a heterologous DNA construct, including a nucleic acid expression cassette that comprises a gene of interest, the regeneration of a population of plants resulting from the insertion of the transferred gene into the genome of the plant and selection of a plant characterized by insertion into a particular genome location. An event is characterized phenotypically by the expression of the inserted gene. At the genetic level, an event is part of the genetic makeup of a plant. The term "event" also refers to progeny produced by a sexual cross between the transformant and another plant wherein the progeny include the heterologous DNA.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al. (1986) Proc. Natl. Acad. Sci. USA 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) EMBO J. 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment", in Plant Cell, Tissue, and Organ Culture: Fundamental Methods, ed. Gamborg and Phillips (Springer-Verlag, Berlin) (maize); McCabe et al. (1988) Biotechnology 6:923-926); and Lecl transformation (WO 00/28058). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P: 175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, New York), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255; Christou and Ford (1995) Annals of Botany 75:407-413 (rice); Osjoda et al. (1996) Nature Biotechnology 14:745-750 (maize via *Agrobacterium tumefaciens*); and US Patent Application Publication Number 2017/0121722 (rapid plant transformation) all of which are herein incorporated by reference in their entireties.

The bacteria-mediated transformation methods provided herein rely upon the use of modified *Agrobacterium* strains to produce regenerable plant cells having an incorporated nucleotide sequence of interest. Bacterial strains useful in the methods of the disclosure include, but are not limited to, disarmed *Agrobacterium* including LBA4404 and LBA4404 THY– in which a Tn904 transposon has been deleted or rendered non-functional. More particularly, bacterial strains useful in the methods of the disclosure include, but are not limited to, disarmed Agrobacteria including LBA4404 and LBA4404 THY– in which both copies of the Tn904 transposon have been deleted or rendered non-functional.

The methods of the disclosure, using the modified *Agrobacterium* strains disclosed herein, involve introducing a polypeptide or polynucleotide into a plant. As used herein, "introducing" means presenting to the plant the polynucleotide or polypeptide in such a manner that the sequence gains access to the interior of a cell of the plant. The methods of the disclosure, using the modified *Agrobacterium* strains disclosed herein, do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods and virus-mediated methods.

A "stable transformation" is a transformation in which the nucleotide construct introduced into a plant integrates into the genome of the plant and is capable of being inherited by the progeny thereof. "Transient transformation" means that a polynucleotide is introduced into the plant and does not integrate into the genome of the plant or a polypeptide is introduced into a plant.

Reporter genes or selectable marker genes may also be included in the expression cassettes and used in the methods of the disclosure, using the modified *Agrobacterium* strains disclosed herein. Examples of suitable reporter genes known in the art can be found in, for example, Jefferson, et al., (1991) in Plant Molecular Biology Manual, ed. Gelvin, et al., (Kluwer Academic Publishers), pp. 1-33; DeWet, et al., (1987) Mol. Cell. Biol. 7:725-737; Goff, et al., (1990) EMBO J. 9:2517-2522; Kain, et al., (1995) Bio Techniques 19:650-655 and Chiu, et al., (1996) Current Biology 6:325-330, herein incorporated by reference in their entirety.

A selectable marker comprises a DNA segment that allows one to identify or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of selectable markers include, but are not limited to, DNA segments that comprise restriction enzyme sites; DNA segments that encode products which provide resistance against otherwise toxic compounds (e.g., antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella, et al., (1983) EMBO J. 2:987-992); methotrexate (Herrera Estrella, et al., (1983) Nature 303:209-213; Meijer, et al., (1991) Plant Mol. Biol. 16:807-820); hygromycin (Waldron, et al., (1985) Plant Mol. Biol. 5:103-108 and Zhijian, et al., (1995) Plant Science 108:219-227); streptomycin (Jones, et al., (1987) Mol. Gen. Genet. 210:86-91); spectinomycin (Bretagne-Sagnard, et al., (1996) Transgenic Res. 5:131-137); bleomycin (Hille, et al., (1990) Plant Mol. Biol. 7:171-176); sulfonamide (Guerineau, et al., (1990) Plant Mol. Biol. 15:127-36); bromoxynil (Stalker, et al., (1988) Science 242:419-423); glyphosate (Shaw, et al., (1986)

Science 233:478-481 and U.S. patent application Ser. Nos. 10/004,357 and 10/427,692); phosphinothricin (DeBlock, et al., (1987) EMBO J. 6:2513-2518), herein incorporated by reference in their entirety.

Selectable markers that confer resistance to herbicidal compounds include genes encoding resistance and/or tolerance to herbicidal compounds, such as glyphosate, sulfonylureas, glufosinate ammonium, bromoxynil, imidazolinones, and 2,4-dichlorophenoxyacetate (2,4-D). See generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Sci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Bairn et al. (1991) Proc. Natl. Acad. Sci. USA 88:5072-5076; Wyborski et al. (1991) Nucleic Acids Res. 19:4647-4653; Hillen and Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

Certain selectable markers useful in the present methods, using the modified *Agrobacterium* strains disclosed herein, include, but are not limited to, the maize HRA gene (Lee et al., 1988, EMBO J 7:1241-1248) which confers resistance to sulfonylureas and imidazolinones, the GAT gene which confers resistance to glyphosate (Castle et al., 2004, Science 304:1151-1154), genes that confer resistance to spectinomycin such as the aadA gene (Svab et al., 1990, Plant Mol Biol. 14:197-205) and the bar gene that confers resistance to glufosinate ammonium (White et al., 1990, Nucl. Acids Res. 25:1062), and PAT (or moPAT for corn, see Rasco-Gaunt et al., 2003, Plant Cell Rep. 21:569-76) and the PMI gene that permits growth on mannose-containing medium (Negrotto et al., 2000, Plant Cell Rep. 22:684-690) are very useful for rapid selection during the brief elapsed time encompassed by somatic embryogenesis and embryo maturation. However, depending on the selectable marker used and the crop, inbred or variety being transformed, the percentage of wild-type escapes can vary. In maize and sorghum, the HRA gene is efficacious in reducing the frequency of wild-type escapes.

Other genes that could have utility in the recovery of transgenic events would include, but are not limited to, examples such as GUS (beta-glucuronidase; Jefferson, (1987) Plant Mol. Biol. Rep. 5:387), GFP (green fluorescence protein; Chalfie, et al., (1994) Science 263:802), luciferase (Riggs, et al., (1987) Nucleic Acids Res. 15(19): 8115 and Luehrsen, et al., (1992) Methods Enzymol. 216: 397-414), various fluorescent proteins with a spectrum of alternative emission optima spanning Far-Red, Red, Orange, Yellow, Green Cyan and Blue (Shaner et al., 2005, Nature Methods 2:905-909) and the maize genes encoding for anthocyanin production (Ludwig, et al., (1990) Science 247:449), herein incorporated by reference in their entireties.

The above list of selectable markers is not meant to be limiting. Any selectable marker can be used in the methods of the disclosure, using the modified *Agrobacterium* strains disclosed herein.

In an aspect, the methods of the disclosure, using the modified *Agrobacterium* strains disclosed herein, provide transformation methods that allow positive growth selection. One skilled in the art can appreciate that conventional plant transformation methods have relied predominantly on negative selection schemes as described above, in which an antibiotic or herbicide (a negative selective agent) is used to inhibit or kill non-transformed cells or tissues, and the transgenic cells or tissues continue to grow due to expression of a resistance gene. In contrast, the methods of the present disclosure, using the modified *Agrobacterium* strains disclosed herein, can be used with no application of a negative selective agent. Thus, although wild-type cells can grow unhindered, by comparison cells impacted by the controlled expression of a morphogenic gene can be readily identified due to their accelerated growth rate relative to the surrounding wild-type tissue. In addition to simply observing faster growth, the methods of the disclosure, using the modified *Agrobacterium* strains disclosed herein, provide transgenic cells that exhibit more rapid morphogenesis relative to non-transformed cells. Accordingly, such differential growth and morphogenic development can be used to easily distinguish transgenic plant structures from the surrounding non-transformed tissue, a process which is termed herein as "positive growth selection".

The present disclosure provides methods, using the modified *Agrobacterium* strains disclosed herein, for producing transgenic plants with increased efficiency and speed and providing significantly higher transformation frequencies and significantly more quality events (events containing one copy of a trait gene cassette with no vector (plasmid) backbone) in multiple inbred lines using a variety of starting tissue types, including transformed inbreds representing a range of genetic diversities and having significant commercial utility. The disclosed methods, using the modified *Agrobacterium* strains disclosed herein, can further comprise polynucleotides that provide for improved traits and characteristics.

As used herein, "trait" refers to a physiological, morphological, biochemical, or physical characteristic of a plant or particular plant material or plant cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring uptake of carbon dioxide, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) Eur. J. Biochem. 165:99-106, the disclosures of which are herein incorporated by reference.

Derivatives of the coding sequences can be made by site-directed mutagenesis to increase the level of preselected amino acids in the encoded polypeptide. For example, methionine-rich plant proteins such as from sunflower seed (Lilley et al. (1989) Proceedings of the World Congress on Vegetable Protein Utilization in Human Foods and Animal Feedstuffs, ed. Applewhite (American Oil Chemists Society, Champaign, Ill.), pp. 497-502; herein incorporated by reference); corn (Pedersen et al. (1986) J. Biol. Chem. 261: 6279; Kirihara et al. (1988) Gene 71:359; both of which are herein incorporated by reference); and rice (Musumura et al. (1989) Plant Mol. Biol. 12:123, herein incorporated by reference) could be used. Other agronomically important genes encode latex, Floury 2, growth factors, seed storage factors, and transcription factors.

Many agronomic traits can affect "yield", including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), ear number, seed number per ear, seed size, composition of seed (starch, oil, protein) and characteristics of seed fill. Also of interest is the generation of transgenic plants that demonstrate desirable phenotypic properties that may or may not confer an increase in overall plant yield. Such properties include enhanced plant morphology, plant physiology or improved components of the mature seed harvested from the transgenic plant.

"Increased yield" of a transgenic plant of the present disclosure may be evidenced and measured in a number of ways, including test weight, seed number per plant, seed weight, seed number per unit area (i.e. seeds, or weight of seeds, per acre), bushels per acre, tons per acre, kilo per hectare. For example, maize yield may be measured as production of shelled corn kernels per unit of production area, e.g. in bushels per acre or metric tons per hectare, often reported on a moisture adjusted basis, e.g., at 15.5% moisture. Increased yield may result from improved utilization of key biochemical compounds, such as nitrogen, phosphorous and carbohydrate, or from improved tolerance to environmental stresses, such as cold, heat, drought, salt, and attack by pests or pathogens. Trait-enhancing recombinant DNA may also be used to provide transgenic plants having improved growth and development, and ultimately increased yield, as the result of modified expression of plant growth regulators or modification of cell cycle or photosynthesis pathways.

An "enhanced trait" as used in describing the aspects of the present disclosure includes improved or enhanced water use efficiency or drought tolerance, osmotic stress tolerance, high salinity stress tolerance, heat stress tolerance, enhanced cold tolerance, including cold germination tolerance, increased yield, improved seed quality, enhanced nitrogen use efficiency, early plant growth and development, late plant growth and development, enhanced seed protein, and enhanced seed oil production.

Any polynucleotide of interest can be used in the methods of the disclosure, using the modified *Agrobacterium* strains disclosed herein. Various changes in phenotype, imparted by a gene of interest, include those for modifying the fatty acid composition in a plant, altering the amino acid content, starch content, or carbohydrate content of a plant, altering a plant's pathogen defense mechanism, altering kernel size, altering sucrose loading, and the like. The gene of interest may also be involved in regulating the influx of nutrients, and in regulating expression of phytate genes particularly to lower phytate levels in the seed. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as the understanding of agronomic traits and characteristics such as yield and heterosis increase, the choice of genes for transformation will change accordingly. General categories of nucleotide sequences or genes of interest useful in the methods of the disclosure, using the modified *Agrobacterium* strains disclosed herein, include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, environmental stress resistance (altered tolerance to cold, salt, drought, etc.), grain characteristics, and commercial products.

Heterologous coding sequences, heterologous polynucleotides, and polynucleotides of interest expressed by a promoter sequence transformed by the methods disclosed herein, using the modified *Agrobacterium* strains disclosed herein, may be used for varying the phenotype of a plant. Various changes in phenotype are of interest including modifying expression of a gene in a plant, altering a plant's pathogen or insect defense mechanism, increasing a plant's tolerance to herbicides, altering plant development to respond to environmental stress, modulating the plant's response to salt, temperature (hot and cold), drought and the like. These results can be achieved by the expression of a heterologous nucleotide sequence of interest comprising an appropriate gene product. In specific aspects, the heterologous nucleotide sequence of interest is an endogenous plant sequence whose expression level is increased in the plant or plant part. Results can be achieved by providing for altered expression of one or more endogenous gene products, particularly hormones, receptors, signaling molecules, enzymes, transporters or cofactors or by affecting nutrient uptake in the plant. These changes result in a change in phenotype of the transformed plant. Still other categories of transgenes include genes for inducing expression of exogenous products such as enzymes, cofactors, and hormones from plants and other eukaryotes as well as prokaryotic organisms.

It is recognized that any gene of interest, polynucleotide of interest, or multiple genes/polynucleotides of interest can be operably linked to a promoter or promoters and expressed in a plant transformed by the methods disclosed herein, using the modified *Agrobacterium* strains disclosed herein, for example insect resistance traits which can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like).

A promoter can be operably linked to agronomically important traits for expression in plants transformed by the methods disclosed herein, using the modified *Agrobacterium* strains disclosed herein, that affect quality of grain, such as levels (increasing content of oleic acid) and types of oils, saturated and unsaturated, quality and quantity of essential amino acids, increasing levels of lysine and sulfur, levels of cellulose, and starch and protein content. A promoter can be operably linked to genes providing hordothionin protein modifications for expression in plants transformed by the methods disclosed herein, using the modified *Agrobacterium* strains disclosed herein, which are described in U.S. Pat. Nos. 5,990,389; 5,885,801; 5,885,802 and 5,703,049; herein incorporated by reference in their entirety. Another example of a gene to which a promoter can be operably linked to for expression in plants transformed by the methods disclosed herein, using the modified *Agrobacterium* strains disclosed herein, is a lysine and/or sulfur rich seed protein encoded by the soybean 2S albumin described in U.S. Pat. No. 5,850,016, and the chymotrypsin inhibitor from barley, Williamson, et al., (1987) Eur. J. Biochem 165:99-106, the disclosures of which are herein incorporated by reference in their entirety.

A promoter can be operably linked to insect resistance genes that encode resistance to pests that have yield drag such as rootworm, cutworm, European corn borer and the like for expression in plants transformed by the methods disclosed herein, using the modified *Agrobacterium* strains disclosed herein. Such genes include, for example, *Bacillus thuringiensis* toxic protein genes, U.S. Pat. Nos. 5,366,892; 5,747,450; 5,736,514; 5,723,756; 5,593,881 and Geiser, et al., (1986) Gene 48:109, the disclosures of which are herein incorporated by reference in their entirety. Genes encoding disease resistance traits that can be operably linked to a promoter for expression in plants transformed by the methods disclosed herein, using the modified *Agrobacterium* strains disclosed herein, include, for example, detoxification genes, such as those which detoxify fumonisin (U.S. Pat. No. 5,792,931); avirulence (avr) and disease resistance (R) genes (Jones, et al., (1994) Science 266:789; Martin, et al., (1993) Science 262:1432; and Mindrinos, et al., (1994) Cell 78:1089), herein incorporated by reference in their entirety.

Herbicide resistance traits that can be operably linked to a promoter for expression in plants transformed by the methods disclosed herein, using the modified *Agrobacterium* strains disclosed herein, include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), genes coding for resistance to glyphosate (e.g., the EPSPS gene and the GAT gene; see, for example, US Patent Application Publication Number 2004/0082770, WO 03/092360 and WO 05/012515, herein incorporated by reference in their entirety) or other such genes known in the art. The bar gene encodes resistance to the herbicide basta, the nptII gene encodes resistance to the antibiotics kanamycin and geneticin and the ALS-gene mutants encode resistance to the herbicide chlorsulfuron any and all of which can be operably linked to a promoter for expression in plants transformed by the methods disclosed herein, using the modified *Agrobacterium* strains disclosed herein.

Glyphosate resistance is imparted by mutant 5-enolpyruvl-3-phosphikimate synthase (EPSPS) and aroA genes which can be operably linked to a promoter for expression in plants transformed by the methods disclosed herein, using the modified *Agrobacterium* strains disclosed herein. See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes which can be operably linked to a promoter for expression in plants transformed by the methods disclosed herein, using the modified *Agrobacterium* strains disclosed herein. See also, U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and international publications WO 97/04103; WO 97/04114; WO 00/66746; WO 01/66704; WO 00/66747 and WO 00/66748, which are incorporated herein by reference in their entirety. Glyphosate resistance is also imparted to plants that express a gene which can be operably linked to a promoter for expression in plants transformed by the methods disclosed herein, using the modified *Agrobacterium* strains disclosed herein, that encodes a glyphosate oxido-reductase enzyme as described more fully in U.S. Pat. Nos. 5,776,760 and 5,463,175, which are incorporated herein by reference in their entirety. Glyphosate resistance can also be imparted to plants by the over expression of genes which can be operably linked to a promoter for expression in plants transformed by the methods disclosed herein, using the modified *Agrobacterium* strains disclosed herein, encoding glyphosate N-acetyltransferase. See, for example, US Patent Application Publication Number 2004/0082770, WO 03/092360 and WO 05/012515, herein incorporated by reference in their entirety.

Sterility genes operably linked to a promoter for expression in plants transformed by the methods disclosed herein, using the modified *Agrobacterium* strains disclosed herein, can also be encoded in a DNA construct and provide an alternative to physical detasseling. Examples of genes used in such ways include male tissue-preferred genes and genes with male sterility phenotypes such as QM, described in U.S. Pat. No. 5,583,210, herein incorporated by reference in its entirety. Other genes which can be operably linked to a promoter for expression in plants transformed by the methods disclosed herein, using the modified *Agrobacterium* strains disclosed herein, include kinases and those encoding compounds toxic to either male or female gametophytic development.

Commercial traits can also be produced using the methods of the disclosure that could increase for example, starch for ethanol production, or provide expression of proteins. Another important commercial use of transformed plants is the production of polymers and bioplastics such as described in U.S. Pat. No. 5,602,321, herein incorporated by reference in its entirety. Genes such as β-Ketothiolase, PHBase (poly-hydroxybutyrate synthase), and acetoacetyl-CoA reductase which can be operably linked to a promoter and used in the methods of the disclosure (see, Schubert, et al., (1988) *J.*

*Bacteriol.* 170:5837-5847, herein incorporated by reference in its entirety) facilitate expression of polyhydroxyalkanoates (PHAs).

Numerous trait genes (heterologous polynucleotides or nucleotide sequences of interest) are known in the art and can be used in the methods disclosed herein. By way of illustration, without intending to be limiting, trait genes (heterologous polynucleotides) that confer resistance to insects or diseases, trait genes (heterologous polynucleotides) that confer resistance to a herbicide, trait genes (heterologous polynucleotides) that confer or contribute to an altered grain characteristic, such as altered fatty acids, altered phosphorus content, altered carbohydrates or carbohydrate composition, altered antioxidant content or composition, or altered essential seed amino acids content or composition are examples of the types of trait genes (heterologous polynucleotides) which can be operably linked to a promoter for expression in plants transformed by the methods disclosed herein. Additional genes known in the art may be included in the expression cassettes useful in the methods disclosed herein. Non-limiting examples include genes that create a site for site specific DNA integration, genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress, or other genes and transcription factors that affect plant growth and agronomic traits such as yield, flowering, plant growth and/or plant structure.

As used herein, "antisense orientation" includes reference to a polynucleotide sequence that is operably linked to a promoter in an orientation where the antisense strand is transcribed. The antisense strand is sufficiently complementary to an endogenous transcription product such that translation of the endogenous transcription product is often inhibited. "Operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

A heterologous nucleotide sequence operably linked to a promoter and its related biologically active fragments or variants useful in the methods disclosed herein, using the modified *Agrobacterium* strains disclosed herein, may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The anti sense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides or greater may be used. Thus, a promoter may be operably linked to antisense DNA sequences to reduce or inhibit expression of a native protein in the plant when transformed by the methods disclosed herein, using the modified *Agrobacterium* strains disclosed herein.

"RNAi" refers to a series of related techniques to reduce the expression of genes (see, for example, U.S. Pat. No. 6,506,559, herein incorporated by reference in its entirety). Older techniques referred to by other names are now thought to rely on the same mechanism but are given different names in the literature. These include "antisense inhibition," the production of antisense RNA transcripts capable of suppressing the expression of the target protein and "co-suppression" or "sense-suppression," which refer to the production of sense RNA transcripts capable of suppressing the expression of identical or substantially similar foreign or endogenous genes (U.S. Pat. No. 5,231,020, incorporated herein by reference in its entirety). Such techniques rely on the use of constructs resulting in the accumulation of double stranded RNA with one strand complementary to the target gene to be silenced.

As used herein, the terms "promoter" or "transcriptional initiation region" mean a regulatory region of DNA usually comprising a TATA box or a DNA sequence capable of directing RNA polymerase II to initiate RNA synthesis at the appropriate transcription initiation site for a particular coding sequence. A promoter may additionally comprise other recognition sequences generally positioned upstream or 5' to the TATA box or the DNA sequence capable of directing RNA polymerase II to initiate RNA synthesis, referred to as upstream promoter elements, which influence the transcription initiation rate.

The transcriptional initiation region, the promoter, may be native or homologous or foreign or heterologous to the host, or could be the natural sequence or a synthetic sequence. By foreign is intended that the transcriptional initiation region is not found in the wild-type host into which the transcriptional initiation region is introduced. Either a native or heterologous promoter may be used with respect to the coding sequence of interest.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the potato proteinase inhibitor (PinII) gene or sequences from Ti-plasmid of *A. tumefaciens*, such as the nopaline synthase, octopine synthase and opaline synthase termination regions. See also, Guerineau et al., (1991) Mol. Gen. Genet. 262: 141-144; Proudfoot (1991) Cell 64: 671-674; Sanfacon et al. (1991) Genes Dev. 5: 141-149; Mogen et al. (1990) Plant Cell 2: 1261-1272; Munroe et al. (1990) Gene 91: 151-158; Ballas et al. 1989) Nucleic Acids Res. 17: 7891-7903; Joshi et al. (1987) Nucleic Acid Res. 15: 9627-9639.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5'noncoding region) (Elroy-Stein, O., Fuerst, T. R., and Moss, B. (1989) PNAS USA, 86: 6126-6130); potyvirus leaders, for example, TEV leader (Tobacco Etch Virus) (Allison et al. (1986); MDMV leader (Maize Dwarf Mosaic Virus); Virology, 154: 9-20), and human immunoglobulin heavy-chain binding protein (BiP), (Macejak, D. G., and P. Sarnow (1991) Nature, 353: 90-94; untranslated leader from the coat protein MARNA of alfalfa mosaic virus (AMV RNA 4), (Jobling, S. A., and Gehrke, L., (1987) Nature, 325: 622-625; tobacco mosaic virus leader (TMV), (Gallie et al. (1989) Molecular Biology of RNA, pages 237-256, Gallie et al. (1987) Nucl. Acids Res. 15: 3257-3273; maize chlorotic mottle virus leader (MCMV) (Lornmel, S. A. et al. (1991) Virology, 81: 382-385). See also, Della-Cioppa et al. (1987) Plant Physiology, 84: 965-968; and endogenous maize 5' untranslated sequences. Other methods known to enhance translation can also be utilized, for example, introns, and the like.

The expression cassettes may contain one or more than one gene or nucleic acid sequence to be transferred and expressed in the transformed plant. Thus, each nucleic acid sequence will be operably linked to 5' and 3' regulatory sequences. Alternatively, multiple expression cassettes may be provided.

A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as from *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissues are referred to as "tissue specific". A "cell type" specific promoter primarily drives expression in certain cell types in one or more organs, for example, vascular cells in roots or leaves. Tissue specific, tissue preferred, cell type specific, and inducible promoters constitute the class of "non-constitutive" promoters.

An "inducible" or "repressible" promoter can be a promoter which is under either environmental or exogenous control. Examples of environmental conditions that may affect transcription by inducible promoters include anaerobic conditions, or certain chemicals, or the presence of light. Alternatively, exogenous control of an inducible or repressible promoter can be affected by providing a suitable chemical or other agent that via interaction with target polypeptides result in induction or repression of the promoter. Inducible promoters include heat-inducible promoters, estradiol-responsive promoters, chemical inducible promoters, and the like. Pathogen inducible promoters include those from pathogenesis-related proteins (PR proteins), which are induced following infection by a pathogen; e. g., PR proteins, SAR proteins, beta-1,3-glucanase, chitinase, etc. See, for example, Redolfi et al. (1983) Neth. J. Plant Pathol. 89: 245-254; Uknes et al. (1992) The Plant Cell 4: 645-656; and Van Loon (1985) Plant Mol. Virol. 4: 111-116. Inducible promoters useful in the present methods, using the modified *Agrobacterium* strains disclosed herein, include GLB1, OLE, LTP2, HSP17.7, HSP26, HSP18A, and XVE promoters.

A chemically-inducible promoter can be repressed by the tetracycline repressor (TETR), the ethametsulfuron repressor (ESR), or the chlorsulfuron repressor (CR), and de-repression occurs upon addition of tetracycline-related or sulfonylurea ligands. The repressor can be TETR and the tetracycline-related ligand is doxycycline or anhydrotetracycline. (Gatz, C., Frohberg, C. and Wendenburg, R. (1992) Stringent repression and homogeneous de-repression by tetracycline of a modified CaMV 35S promoter in intact transgenic tobacco plants, Plant J. 2, 397-404). Alternatively, the repressor can be ESR and the sulfonylurea ligand is ethametsulfuron, chlorsulfuron, metsulfuron-methyl, sulfometuron methyl, chlorimuron ethyl, nicosulfuron, primisulfuron, tribenuron, sulfosulfuron, trifloxysulfuron, foramsulfuron, iodosulfuron, prosulfuron, thifensulfuron, rimsulfuron, mesosulfuron, or halosulfuron (US20110287936 incorporated herein by reference in its entirety). If the repressor is CR, the CR ligand is chlorsulfuron. See, U.S. Pat. No. 8,580,556 incorporated herein by reference in its entirety.

A "constitutive" promoter is a promoter which is active under most conditions. Promoters useful in the present disclosure include those disclosed in WO2017/112006 and those disclosed in U.S. Provisional Application 62/562,663. Constitutive promoters for use in expression of genes in plants are known in the art. Such promoters include but are not limited to 35S promoter of cauliflower mosaic virus (Depicker et al. (1982) Mol. Appl. Genet. 1: 561-573; Odell et al. (1985) Nature 313: 810-812), ubiquitin promoter (Christensen et al. (1992) Plant Mol. Biol. 18: 675-689), promoters from genes such as ribulose bisphosphate carboxylase (De Almeida et al. (1989) Mol. Gen. Genet. 218: 78-98), actin (McElroy et al. (1990) Plant J. 2: 163-171), histone, DnaJ (Baszczynski et al. (1997) Maydica 42: 189-201), and the like.

As used herein, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements that modify gene expression. It is to be understood that nucleotide sequences, located within introns or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the methods of the disclosure, using the modified *Agrobacterium* strains disclosed herein, a post-transcriptional regulatory element may include elements that are active following transcription initiation, for example translational and transcriptional enhancers, translational and transcriptional repressors and mRNA stability determinants.

A "heterologous nucleotide sequence", "heterologous polynucleotide of interest", or "heterologous polynucleotide" as used throughout the disclosure, is a sequence that is not naturally occurring with or operably linked to a promoter. While this nucleotide sequence is heterologous to the promoter sequence, it may be homologous or native or heterologous or foreign to the plant host. Likewise, the promoter sequence may be homologous or native or heterologous or foreign to the plant host and/or the polynucleotide of interest.

The DNA constructs and expression cassettes useful in the methods of the disclosure, using the modified *Agrobacte-*

*rium* strains disclosed herein, can also include further enhancers, either translation or transcription enhancers, as may be required. These enhancer regions are well known to persons skilled in the art and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene and can be specifically modified to increase translation of the mRNA. It is recognized that to increase transcription levels enhancers may be utilized in combination with promoter regions. It is recognized that to increase transcription levels, enhancers may be utilized in combination with promoter regions. Enhancers are nucleotide sequences that act to increase the expression of a promoter region. Enhancers are known in the art and include the SV40 enhancer region, the 35S enhancer element and the like. Some enhancers are also known to alter normal promoter expression patterns, for example, by causing a promoter to be expressed constitutively when without the enhancer, the same promoter is expressed only in one specific tissue or a few specific tissues.

Generally, a "weak promoter" means a promoter that drives expression of a coding sequence at a low level. A "low level" of expression is intended to mean expression at levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts.

It is recognized that sequences useful in the methods of the disclosure, using the modified *Agrobacterium* strains disclosed herein, may be used with their native coding sequences thereby resulting in a change in phenotype of the transformed plant. The morphogenic genes and genes of interest disclosed herein, as well as variants and fragments thereof, are useful in the methods of the disclosure, using the modified *Agrobacterium* strains disclosed herein, for the genetic manipulation of any plant. The term "operably linked" means that the transcription or translation of a heterologous nucleotide sequence is under the influence of a promoter sequence.

In one aspect of the disclosure, expression cassettes comprise a transcriptional initiation region or variants or fragments thereof, operably linked to a morphogenic gene and/or a heterologous nucleotide sequence. Such expression cassettes can be provided with a plurality of restriction sites for insertion of the nucleotide sequence to be under the transcriptional regulation of the regulatory regions. The expression cassettes may additionally contain selectable marker genes as well as 3' termination regions.

The expression cassettes can include, in the 5'-3' direction of transcription, a transcriptional initiation region (i.e., a promoter, or variant or fragment thereof), a translational initiation region, a heterologous nucleotide sequence of interest, a translational termination region and optionally, a transcriptional termination region functional in the host organism. The regulatory regions (i.e., promoters, transcriptional regulatory regions, and translational termination regions), the polynucleotide of interest useful in the methods of the disclosure, using the modified *Agrobacterium* strains disclosed herein, may be native/analogous to the host cell or to each other. Alternatively, the regulatory regions, the polynucleotide of interest may be heterologous to the host cell or to each other. As used herein, "heterologous" in reference to a sequence is a sequence that originates from a foreign species or, if from the same species, is substantially modified from its native form in composition and/or genomic locus by deliberate human intervention. For example, a promoter operably linked to a heterologous polynucleotide is from a species different from the species from which the polynucleotide was derived or, if from the same/analogous species, one or both are substantially modified from their original form and/or genomic locus or the promoter is not the native promoter for the operably linked polynucleotide.

The termination region may be native with the transcriptional initiation region, may be native with the operably linked DNA sequence of interest, may be native with the plant host, or may be derived from another source (i.e., foreign or heterologous to the promoter, the morphogenic gene and/or the DNA sequence being expressed, the plant host, or any combination thereof). Convenient termination regions are available from the Ti-plasmid of *A. tumefaciens*, such as the octopine synthase and nopaline synthase termination regions. See also, Guerineau, et al., (1991) Mol. Gen. Genet. 262:141-144; Proudfoot, (1991) Cell 64:671-674; Sanfacon, et al., (1991) Genes Dev. 5:141-149; Mogen, et al., (1990) Plant Cell 2:1261-1272; Munroe, et al., (1990) Gene 91:151-158; Ballas, et al., (1989) Nucleic Acids Res. 17:7891-7903; and Joshi, et al., (1987) Nucleic Acid Res. 15:9627-9639, herein incorporated by reference in their entirety.

An expression cassette comprising a promoter operably linked to a heterologous nucleotide sequence, a heterologous polynucleotide of interest, a heterologous polynucleotide nucleotide, or a sequence of interest can be used to transform any plant. Alternatively, a heterologous polynucleotide of interest, a heterologous polynucleotide nucleotide, or a sequence of interest operably linked to a promoter can be on a separate expression cassette positioned outside of the transfer-DNA. In this manner, genetically modified plants, plant cells, plant tissue, seed, root and the like can be obtained. The expression cassette may also contain at least one additional nucleotide sequence for a gene, heterologous nucleotide sequence, heterologous polynucleotide of interest, or heterologous polynucleotide to be cotransformed into the organism. Alternatively, the additional nucleotide sequence(s) can be provided on another expression cassette.

Where appropriate, the nucleotide sequences whose expression is to be under the control a promoter sequence and any additional nucleotide sequence(s) may be optimized for increased expression in the transformed plant. That is, these nucleotide sequences can be synthesized using plant preferred codons for improved expression. See, for example, Campbell and Gowri, (1990) Plant Physiol. 92:1-11, herein incorporated by reference in its entirety, for a discussion of host-preferred codon usage. Methods are available in the art for synthesizing plant-preferred genes. See, for example, U.S. Pat. Nos. 5,380,831, 5,436,391 and Murray, et al., (1989) Nucleic Acids Res. 17:477-498, herein incorporated by reference in their entirety.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of a heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes useful in the methods of the disclosure, using the modified *Agrobacterium* strains disclosed herein, may additionally contain 5' leader sequences. Such leader sequences can act to enhance translation. Translation leaders are known in the art and include, without limitation: picornavirus leaders, for example, EMCV leader (Encephalomycarditis 5' noncoding region) (Elroy-Stein, et al., (1989) Proc. Nat. Acad. Sci. USA 86:6126-6130); potyvirus leaders, for example, TEV leader (Tobacco Etch Virus) (Allison, et al., (1986) Virology 154:9-20); MDMV leader (Maize Dwarf Mosaic Virus); human immunoglobulin heavy-chain binding protein (BiP) (Macejak, et al., (1991) Nature 353:90-94); untranslated leader from the coat protein mRNA of alfalfa mosaic virus (AMV RNA 4) (Jobling, et al., (1987) Nature 325:622-625); tobacco mosaic virus leader (TMV) (Gallie, et al., (1989) Molecular Biology of RNA, pages 237-256) and maize chlorotic mottle virus leader (MCMV) (Lommel, et al., (1991) Virology 81:382-385), herein incorporated by reference in their entirety. See, also, Della-Cioppa, et al., (1987) Plant Physiology 84:965-968, herein incorporated by reference in its entirety. Methods known to enhance mRNA stability can also be utilized, for example, introns, such as the maize Ubiquitin intron (Christensen and Quail, (1996) Transgenic Res. 5:213-218; Christensen, et al., (1992) Plant Molecular Biology 18:675-689) or the maize Adhl intron (Kyozuka, et al., (1991) Mol. Gen. Genet. 228:40-48; Kyozuka, et al., (1990) Maydica 35:353-357) and the like, herein incorporated by reference in their entirety.

In preparing expression cassettes useful in the methods of the disclosure, using the modified *Agrobacterium* strains disclosed herein, the various DNA fragments may be manipulated, to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, for example, transitions and transversions, may be involved.

As used herein, "vector" refers to a DNA molecule such as a plasmid, cosmid or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

Cells that have been transformed may be grown into plants in accordance with conventional ways. See, for example, McCormick, et al., (1986) Plant Cell Reports 5:81-84, herein incorporated by reference in its entirety. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a nucleotide construct useful in the methods of the disclosure, using the modified *Agrobacterium* strains disclosed herein, for example, an expression cassette useful in the methods of the disclosure, using the modified *Agrobacterium* strains disclosed herein, stably incorporated into its genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif., herein incorporated by reference in its entirety). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant produced by the methods of the disclosure, using the modified *Agrobacterium* strains disclosed herein, containing a desired polynucleotide of interest is cultivated using methods well known to one skilled in the art.

Methods are known in the art for the targeted insertion of a polynucleotide at a specific location in the plant genome. The insertion of the polynucleotide at a desired genomic location is achieved using a site-specific recombination system. See, for example, U.S. Pat. No. 9,222,098 B2, U.S. Pat. No. 7,223,601 B2, U.S. Pat. No. 7,179,599 B2, and U.S. Pat. No. 6,911,575 B1, all of which are herein incorporated by reference in their entirety. Briefly, a polynucleotide of interest, flanked by two non-identical recombination sites, can be contained in a T-DNA transfer cassette. The T-DNA transfer cassette is introduced into a plant having stably incorporated into its genome a target site which is flanked by two non-identical recombination sites that correspond to the sites of the transfer cassette. An appropriate recombinase is provided, and the transfer cassette is integrated at the target site. The polynucleotide of interest is thereby integrated at a specific chromosomal position in the plant genome.

In an aspect, the modified *Agrobacterium* strains disclosed herein, can be used to introduce into explants polynucleotides that are useful to target a specific site for modification in the genome of a plant derived from the explant. Site specific modifications that can be introduced with the disclosed methods, using the modified *Agrobacterium* strains disclosed herein, include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. For example, the disclosed methods, using the modified *Agrobacterium* strains disclosed herein, can be used to introduce a CRISPR-Cas system into a plant cell or plant, for the purpose of genome modification of a target sequence in the genome of a plant or plant cell, for selecting plants, for deleting a base or a sequence, for gene editing, and for inserting a polynucleotide of interest into the genome of a plant or plant cell. Thus, the disclosed methods, using the modified *Agrobacterium* strains disclosed herein, can be used together with a CRISPR-Cas system to provide for an effective system for modifying or altering target sites and nucleotides of interest within the genome of a plant, plant cell or seed. The Cas endonuclease gene is a plant optimized Cas9 endonuclease, wherein the plant optimized Cas9 endonuclease is capable of binding to and creating a double strand break in a genomic target sequence of the plant genome.

The Cas endonuclease is guided by the guide nucleotide to recognize and optionally introduce a double strand break at a specific target site into the genome of a cell. The CRISPR-Cas system provides for an effective system for modifying target sites within the genome of a plant, plant cell or seed. Further provided are methods, using the modified *Agrobacterium* strains disclosed herein, employing a guide polynucleotide/Cas endonuclease system to provide an effective system for modifying target sites within the genome of a cell and for editing a nucleotide sequence in the genome of a cell. Once a genomic target site is identified, a variety of methods, using the modified *Agrobacterium* strains disclosed herein, can be employed to further modify the target sites such that they contain a variety of polynucleotides of interest. The disclosed methods, using the modified *Agrobacterium* strains disclosed herein, can be used to introduce a CRISPR-Cas system for editing a nucleotide sequence in the genome of a cell. The nucleotide sequence to be edited (the nucleotide sequence of interest) can be located within or outside a target site that is recognized by a Cas endonuclease.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR—repeats) which are partially palindromic. The repeated sequences (usually specific to a species) are interspaced by variable sequences of constant length (typically 20 to 58 by depending on the CRISPR locus (WO2007/025097 published Mar. 1, 2007).

Cas gene includes a gene that is generally coupled, associated or close to or in the vicinity of flanking CRISPR loci. The terms "Cas gene" and "CRISPR-associated (Cas) gene" are used interchangeably herein.

In another aspect, the Cas endonuclease gene is operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region.

As related to the Cas endonuclease, the terms "functional fragment", "fragment that is functionally equivalent", and "functionally equivalent fragment" are used interchangeably herein. These terms refer to a portion or subsequence of the Cas endonuclease sequence in which the ability to create a double-strand break is retained.

As related to the Cas endonuclease, the terms "functional variant", "variant that is functionally equivalent" and "functionally equivalent variant" are used interchangeably herein. These terms refer to a variant of the Cas endonuclease in which the ability to create a double-strand break is retained. Fragments and variants can be obtained via methods such as site-directed mutagenesis and synthetic construction.

In an aspect, the Cas endonuclease gene is a plant codon optimized *Streptococcus pyogenes* Cas9 gene that can recognize any genomic sequence of the form N(12-30)NGG which can in principle be targeted.

Endonucleases are enzymes that cleave the phosphodiester bond within a polynucleotide chain and include restriction endonucleases that cleave DNA at specific sites without damaging the bases. Restriction endonucleases include Type I, Type II, Type III, and Type W endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more (Patent application PCT/US 12/30061 filed on Mar. 22, 2012). Meganucleases have been classified into four families based on conserved sequence motifs. These motifs participate in the coordination of metal ions and hydrolysis of phosphodiester bonds. Meganucleases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families. TAL effector nucleases are a new class of sequence-specific nucleases that can be used to make double-strand breaks at specific target sequences in the genome of a plant or other organism. (Miller, et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type Ms endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18-nucleotide recognition sequence.

A "Dead-CAS9" (dCAS9) as used herein, is used to supply a transcriptional repressor domain. The dCAS9 has been mutated so that can no longer cut DNA. The dCASO can still bind when guided to a sequence by the gRNA and can also be fused to repressor elements. The dCAS9 fused to the repressor element, as described herein, is abbreviated to dCAS9~REP, where the repressor element (REP) can be any of the known repressor motifs that have been characterized in plants. An expressed guide RNA (gRNA) binds to the dCAS9~REP protein and targets the binding of the dCAS9-REP fusion protein to a specific predetermined nucleotide sequence within a promoter (a promoter within the T-DNA). For example, if this is expressed beyond—the border using a ZM-UBI PRO::dCAS9~REP::PINII TERM cassette along with a U6-POL PRO::gRNA::U6 TERM cassette and the gRNA is designed to guide the dCAS9-REP protein to bind the SB-UBI promoter in the expression cassette SB-UBI PRO::moPAT::PINII TERM within the T-DNA, any event that has integrated the beyond-the-border sequence would be bialaphos sensitive. Transgenic events that integrate only the T-DNA would express moPAT and be bialaphos resistant. The advantage of using a dCAS9 protein fused to a repressor (as opposed to a TETR or ESR) is the ability to target these repressors to any promoter within the T-DNA. TETR and ESR are restricted to cognate operator binding sequences. Alternatively, a synthetic Zinc-Finger Nuclease fused to a repressor domain can be used in place of the gRNA and dCAS9~REP (Urritia et al., 2003, Genome Biol. 4:231) as described above.

The type II CRISPR/Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target. As used herein, the term "guide nucleotide" relates to a synthetic fusion of two RNA molecules, a crRNA (CRISPR RNA) comprising a variable targeting domain, and a tracrRNA. In an aspect, the guide nucleotide comprises a variable targeting domain of 12 to 30 nucleotide sequences and a RNA fragment that can interact with a Cas endonuclease.

As used herein, the term "guide polynucleotide" relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited to, Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide nucleotide".

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In an aspect, the guide nucleotide and Cas endonuclease are capable of forming a complex that enables the Cas endonuclease to introduce a double strand break at a DNA target site.

In an aspect of the disclosure the variable target domain is 12, 13, 14, 15, 16, 17, 18, 19, 20, 21, 22, 23, 24, 25, 26, 27, 28, 29 or 30 nucleotides in length.

In an aspect of the disclosure, the guide nucleotide comprises a cRNA (or cRNA fragment) and a tracrRNA (or tracrRNA fragment) of the type II CRISPR/Cas system that can form a complex with a type II Cas endonuclease, wherein the guide nucleotide Cas endonuclease complex can direct the Cas endonuclease to a plant genomic target site, enabling the Cas endonuclease to introduce a double strand break into the genomic target site. The guide nucleotide can be introduced into a plant or plant cell directly using any method known in the art such as, but not limited to, particle bombardment, topical applications, or using the modified *Agrobacterium* strains disclosed herein, for *Agrobacterium* transformation.

In an aspect, the guide nucleotide can be introduced indirectly by introducing a recombinant DNA molecule comprising the corresponding guide DNA sequence operably linked to a plant specific promoter that is capable of transcribing the guide nucleotide in the plant cell. The term "corresponding guide DNA" includes a DNA molecule that is identical to the RNA molecule but has a "T" substituted for each "U" of the RNA molecule.

In an aspect, the guide nucleotide is introduced via particle bombardment or using the disclosed methods, using the modified *Agrobacterium* strains disclosed herein, for *Agrobacterium* transformation of a recombinant DNA construct comprising the corresponding guide DNA operably linked to a plant U6 polymerase III promoter. In an aspect, the RNA that guides the RNA Cas9 endonuclease complex, is a duplexed RNA comprising a duplex crRNA-tracrRNA. One advantage of using a guide nucleotide versus a duplexed crRNA-tracrRNA is that only one expression cassette needs to be made to express the fused guide nucleotide.

The terms "target site", "target sequence", "target DNA", "target locus," "genomic target site", "genomic target sequence", and "genomic target locus" are used interchangeably herein and refer to a polynucleotide sequence in the genome (including choroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature.

As used herein, terms "endogenous target sequence" and "native target sequence" are used interchangeably herein to refer to a target sequence that is endogenous or native to the genome of a plant and is at the endogenous or native position of that target sequence in the genome of the plant. In an aspect, the target site can be similar to a DNA recognition site or target site that that is specifically recognized and/or bound by a double-strand break inducing agent such as a LIG3-4 endonuclease (US patent publication 2009/0133152 A1 (published May 21, 2009) or a MS26++ meganuclease (U.S. patent application Ser. No. 13/526,912 filed Jun. 19, 2012).

An "artificial target site" or "artificial target sequence" are used interchangeably herein and refer to a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

An "altered target site", "altered target sequence", "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

In an aspect, the modified *Agrobacterium* strains disclosed herein, can be used to introduce into plants polynucleotides useful for gene suppression of a target gene in a plant. Reduction of the activity of specific genes (also known as gene silencing, or gene suppression) is desirable for several aspects of genetic engineering in plants. Many techniques for gene silencing are well known to one of skill in the art, including but not limited to antisense technology.

In an aspect, the modified *Agrobacterium* strains disclosed herein, can be used to introduce into plants polynucleotides useful for the targeted integration of nucleotide sequences into a plant. For example, the modified *Agrobacterium* strains disclosed herein, can be used to introduce transfer cassettes (T-DNA expression cassettes) comprising nucleotide sequences of interest flanked by non-identical recombination sites are used to transform a plant comprising a target site. In an aspect, the target site contains at least a set of non-identical recombination sites corresponding to those on the transfer cassette (T-DNA expression cassette). The exchange of the nucleotide sequences flanked by the recombination sites is affected by a recombinase. Thus, the modified *Agrobacterium* strains disclosed herein, can be used for the introduction of transfer cassettes (T-DNA expression cassettes) for targeted integration of nucleotide sequences, wherein the transfer cassettes ((T-DNA expression cassettes) which are flanked by non-identical recombination sites recognized by a recombinase that recognizes and implements recombination at the nonidentical recombination sites. Accordingly, the modified *Agrobacterium* strains disclosed herein, can be used to improve efficiency and speed of development of plants containing non-identical recombination sites.

Thus, using the modified *Agrobacterium* strains disclosed herein, can further comprise methods for the directional, targeted integration of exogenous nucleotides into a transformed plant. In an aspect, the disclosed methods, using the modified *Agrobacterium* strains disclosed herein, use novel recombination sites in a gene targeting system which facilitates directional targeting of desired genes and nucleotide sequences into corresponding recombination sites previously introduced into the target plant genome.

In an aspect, a nucleotide sequence flanked by two non-identical recombination sites is introduced into one or more cells of an explant derived from the target organism's genome establishing a target site for insertion of nucleotide sequences of interest. Once a stable plant or cultured tissue is established a second construct, or nucleotide sequence of interest, flanked by corresponding recombination sites as those flanking the target site, is introduced into the stably transformed plant or tissues in the presence of a recombinase protein. This process results in exchange of the nucleotide sequences between the non-identical recombination sites of the target site and the transfer cassette (T-DNA expression cassette).

It is recognized that the transformed plant prepared in this manner may comprise multiple target sites; i. e., sets of non-identical recombination sites. In this manner, multiple manipulations of the target site in the transformed plant are available. By target site in the transformed plant is intended a DNA sequence that has been inserted into the transformed plant's genome and comprises non-identical recombination sites.

Examples of recombination sites for use in methods using the modified *Agrobacterium* strains disclosed herein, are known. The two-micron plasmid found in most naturally occurring strains of *Saccharomyces cerevisiae*, encodes a site-specific recombinase that promotes an inversion of the DNA between two inverted repeats. This inversion plays a central role in plasmid copy-number amplification.

The protein, designated FLP protein, catalyzes site-specific recombination events. The minimal recombination site (FRT) has been defined and contains two inverted 13-base pair (bp) repeats surrounding an asymmetric 8-bp spacer. The FLP protein cleaves the site at the junctions of the repeats and the spacer and is covalently linked to the DNA via a 3'phosphate. Site specific recombinases like FLP cleave and religate DNA at specific target sequences, resulting in a precisely defined recombination between two identical sites. To function, the system needs the recombination sites and the recombinase. No auxiliary factors are needed. Thus, the entire system can be inserted into and function in plant cells. The yeast FLP\FRT site specific recombination system has been shown to function in plants. To date, the system has been utilized for excision of unwanted DNA. See, Lyznik et al. (1993) Nucleic Acid Res. 21: 969-975. In contrast, the present disclosure utilizes non-identical FRTs for the exchange, targeting, arrangement, insertion and control of expression of nucleotide sequences in the plant genome.

In an aspect, a transformed organism of interest, such as an explant from a plant, containing a target site integrated into its genome is needed. The target site is characterized by being flanked by non-identical recombination sites. A targeting cassette is additionally required containing a nucleotide sequence flanked by corresponding non-identical recombination sites as those sites contained in the target site of the transformed organism. A recombinase which recognizes the non-identical recombination sites and catalyzes site-specific recombination is required.

It is recognized that the recombinase can be provided by any means known in the art. That is, it can be provided in the organism or plant cell by transforming the organism with an expression cassette capable of expressing the recombinase in the organism, by transient expression, or by providing messenger RNA (mRNA) for the recombinase or the recombinase protein.

By "non-identical recombination sites" it is intended that the flanking recombination sites are not identical in sequence and will not recombine or recombination between the sites will be minimal. That is, one flanking recombination site may be a FRT site where the second recombination site may be a mutated FRT site. The non-identical recombination sites used in the methods of the disclosure, using the modified *Agrobacterium* strains disclosed herein, prevent or greatly suppress recombination between the two flanking recombination sites and excision of the nucleotide sequence contained therein. Accordingly, it is recognized that any suitable non-identical recombination sites may be utilized in the disclosure, including FRT and mutant FRT sites, FRT and lox sites, lox and mutant lox sites, as well as other recombination sites known in the art.

By suitable non-identical recombination site implies that in the presence of active recombinase, excision of sequences between two non-identical recombination sites occurs, if at all, with an efficiency considerably lower than the recombinationally-mediated exchange targeting arrangement of nucleotide sequences into the plant genome. Thus, suitable non-identical sites for use in the disclosure include those sites where the efficiency of recombination between the sites is low; for example, where the efficiency is less than about 30 to about 50%, preferably less than about 10 to about 30%, more preferably less than about 5 to about 10%.

As noted above, the recombination sites in the targeting cassette correspond to those in the target site of the transformed plant. That is, if the target site of the transformed plant contains flanking non-identical recombination sites of FRT and a mutant FRT, the targeting cassette will contain the same FRT and mutant FRT non-identical recombination sites.

It is furthermore recognized that the recombinase, which is used in the disclosed methods, using the modified *Agrobacterium* strains disclosed herein, will depend upon the recombination sites in the target site of the transformed plant and the targeting cassette. That is, if FRT sites are utilized, the FLP recombinase will be needed. In the same manner, where lox sites are utilized, the Cre recombinase is required. If the non-identical recombination sites comprise both a FRT and a lox site, both the FLP and Cre recombinase will be required in the plant cell.

The FLP recombinase is a protein which catalyzes a site-specific reaction that is involved in amplifying the copy number of the two-micron plasmid of *S. cerevisiae* during DNA replication. FLP protein has been cloned and expressed. See, for example, Cox (1993) Proc. Natl. Acad. Sci. U.S.A 80: 4223-4227. The FLP recombinase for use in the disclosure may be that derived from the genus *Saccharomyces*. It may be preferable to synthesize the recombinase using plant preferred codons for optimum expression in a plant of interest. See, for example, U.S. application Ser. No. 08/972,258 filed Nov. 18, 1997, entitled "Novel Nucleic Acid Sequence Encoding FLP Recombinase", herein incorporated by reference.

The bacteriophage recombinase Cre catalyzes site-specific recombination between two lox sites. The Cre recombinase is known in the art. See, for example, Guo et al. (1997) Nature 389: 40-46; Abremski et al. (1984) J. Biol. Chem. 259: 1509-1514; Chen et al. (1996) Somat. Cell Mol. Genet. 22: 477-488; and Shaikh et al. (1977) J. Biol. Chem. 272: 5695-5702. All of which are herein incorporated by reference. Such Cre sequence may also be synthesized using plant preferred codons.

Where appropriate, the nucleotide sequences to be inserted in the plant genome may be optimized for increased expression in the transformed plant. Where mammalian, yeast, or bacterial genes are used in the disclosure, they can be synthesized using plant preferred codons for improved expression. It is recognized that for expression in monocots, dicot genes can also be synthesized using monocot preferred codons. Methods are available in the art for synthesizing plant preferred genes. See, for example, U.S. Pat. Nos. 5,380,831, 5,436,391, and Murray et al. (1989) Nucleic Acids Res. 17: 477-498, herein incorporated by reference. The plant preferred codons may be determined from the codons utilized more frequently in the proteins expressed in the plant of interest. It is recognized that monocot or dicot preferred sequences may be constructed as well as plant preferred sequences for particular plant species. See, for example, EPA 0359472; EPA 0385962; WO 91/16432; Perlak et al. (1991) Proc. Natl. Acad. Sci. USA, 88: 3324-3328; and Murray et al. (1989) Nucleic Acids Research, 17: 477-498. U.S. Pat. Nos. 5,380,831; 5,436,391; and the like, herein incorporated by reference. It is further recognized that all or any part of the gene sequence may be optimized or synthetic. That is, fully optimized or partially optimized sequences may also be used.

Additional sequence modifications are known to enhance gene expression in a cellular host and can be used in the disclosure. These include elimination of sequences encoding spurious polyadenylation signals, exon-intron splice site signals, transposon-like repeats, and other such well-characterized sequences, which may be deleterious to gene expression. The G-C content of the sequence may be adjusted to levels average for a given cellular host, as calculated by reference to known genes expressed in the host cell. When possible, the sequence is modified to avoid predicted hairpin secondary RNA structures.

The present disclosure also encompasses novel FLP recombination target sites (FRT). The FRT has been identified as a minimal sequence comprising two 13 base pair repeats, separated by an eight 8 base spacer region. The nucleotides in the spacer region can be replaced with a combination of nucleotides, so long as the two 13-base repeats are separated by eight nucleotides. It appears that the actual nucleotide sequence of the spacer is not critical; however, for the practice of the disclosure, some substitutions of nucleotides in the space region may work better than others. The eight-base pair spacer is involved in DNA-DNA pairing during strand exchange. The asymmetry of the region determines the direction of site alignment in the recombination event, which will subsequently lead to either inversion or excision. As indicated above, most of the spacer can be mutated without a loss of function. See, for example, Schlake and Bode (1994) Biochemistry 33: 12746-12751, herein incorporated by reference.

Novel FRT mutant sites can be used in the practice of the disclosed methods, using the modified *Agrobacterium* strains disclosed herein. Such mutant sites may be constructed by PCR-based mutagenesis. Although mutant FRT sites are known (see SEQ ID Nos 2, 3, 4 and 5 of WO1999/025821), it is recognized that other mutant FRT sites may be used in the practice of the disclosure. The present disclosure is not the use of a particular FRT or recombination site, but rather that non-identical recombination sites or FRT sites can be utilized for targeted insertion and expression of nucleotide sequences in a plant genome. Thus, other mutant FRT sites can be constructed and utilized based upon the present disclosure.

As discussed above, bringing genomic DNA containing a target site with non-identical recombination sites together with a vector containing a transfer cassette with corresponding non-identical recombination sites, in the presence of the recombinase, results in recombination. The nucleotide sequence of the transfer cassette located between the flanking recombination sites is exchanged with the nucleotide sequence of the target site located between the flanking recombination sites. In this manner, nucleotide sequences of interest may be precisely incorporated into the genome of the host.

It is recognized that many variations of the disclosure can be practiced. For example, target sites can be constructed having multiple non-identical recombination sites. Thus, multiple genes or nucleotide sequences can be stacked or ordered at precise locations in the plant genome. Likewise, once a target site has been established within the genome, additional recombination sites may be introduced by incorporating such sites within the nucleotide sequence of the transfer cassette and the transfer of the sites to the target sequence. Thus, once a target site has been established, it is possible to subsequently add sites, or alter sites through recombination.

Another variation includes providing a promoter or transcription initiation region operably linked with the target site in an organism. Preferably, the promoter will be 5' to the first recombination site. By transforming the organism with a transfer cassette comprising a coding region, expression of the coding region will occur upon integration of the transfer cassette into the target site. This aspect provides for a method to select transformed cells, particularly plant cells, by providing a selectable marker sequence as the coding sequence.

Other advantages of the present system include the ability to reduce the complexity of integration of transgenes or transferred DNA in an organism by utilizing transfer cassettes as discussed above and selecting organisms with simple integration patterns. In the same manner, preferred sites within the genome can be identified by comparing several transformation events. A preferred site within the genome includes one that does not disrupt expression of essential sequences and provides for adequate expression of the transgene sequence.

The disclosed methods, using the modified *Agrobacterium* strains disclosed herein, also provide for means to combine multiple cassettes at one location within the genome. Recombination sites may be added or deleted at target sites within the genome.

Any means known in the art for bringing the three components of the system together may be used in the disclosure. For example, a plant can be stably transformed to harbor the target site in its genome. The recombinase may be transiently expressed or provided. Alternatively, a nucleotide sequence capable of expressing the recombinase may be stably integrated into the genome of the plant. In the presence of the corresponding target site and the recombinase, the transfer cassette, flanked by corresponding non-identical recombination sites, is inserted into the transformed plant's genome.

Alternatively, the components of the system may be brought together by sexually crossing transformed plants. In this aspect, a transformed plant, parent one, containing a target site integrated in its genome can be sexually crossed with a second plant, parent two, that has been genetically transformed with a transfer cassette containing flanking non-identical recombination sites, which correspond to those in plant one. Either plant one or plant two contains within its genome a nucleotide sequence expressing recombinase. The recombinase may be under the control of a constitutive or inducible promoter. In this manner, expression of recombinase and subsequent activity at the recombination sites can be controlled.

The disclosed methods, using the modified *Agrobacterium* strains disclosed herein, are useful in targeting the integration of transferred nucleotide sequences to a specific chromosomal site. The nucleotide sequence may encode any nucleotide sequence of interest. Particular genes of interest include those which provide a readily analyzable functional feature to the host cell and/or organism, such as marker genes, as well as other genes that alter the phenotype of the recipient cells, and the like. Thus, genes effecting plant growth, height, susceptibility to disease, insects, nutritional value, and the like may be utilized in the disclosure. The nucleotide sequence also may encode an 'antisense' sequence to turn off or modify gene expression.

It is recognized that the nucleotide sequences will be utilized in a functional expression unit or cassette. By functional expression unit or cassette is intended, the nucleotide sequence of interest with a functional promoter, and in most instances a termination region. There are various ways to achieve the functional expression unit within the practice of the disclosure. In one aspect of the disclosure, the nucleic acid of interest is transferred or inserted into the genome as a functional expression unit.

Alternatively, the nucleotide sequence may be inserted into a site within the genome which is 3' to a promoter region. In this latter instance, the insertion of the coding sequence 3' to the promoter region is such that a functional expression unit is achieved upon integration. The expression cassette (T-DNA expression cassette) will comprise a transcriptional initiation region, or promoter, operably linked to the nucleic acid encoding the peptide of interest. Such an expression cassette is provided with a plurality of restriction sites for insertion of the gene or genes of interest to be under the transcriptional regulation of the regulatory regions.

EXPERIMENTAL

Example 1: Sequences and Plasmids

Sequences useful in the methods of making the modified *Agrobacterium* strains disclosed herein are listed in Table 1 below.

TABLE 1

| SEQ ID NO: | Polynucleotide (DNA) or Polypeptide (PRT) | Name | Description |
| --- | --- | --- | --- |
| 1 | DNA | At.P1 PCR primer | GCCAGGGTTTTCTGAGATCCGTC |
| 2 | DNA | At.P2 PCR primer | CACTGTTATAATAGCTGGATGCT TGCTGTAC |
| 3 | DNA | Ti.P1 PCR primer | TCAGCATATGCAACAGATTCAGC AC |
| 4 | DNA | Ti.P2 PCR primer | CTTTCCTATAGCAAAGGAGGCTT TCTC |
| 5 | DNA | At Deletion (with N) | CGCGAACCCGGGCGCGAAGAGC GCAAAAGCGGTCACAGGCGACGT TCTGGCAAAGCTGCTTGCGACTT GCGAGTCAGACAGCCTGCGCGAT CTACGCGACAAGGCAATCCTGAT GGTGGCCTTTGCCTCGGGCGGCC GGCGGCGCAGCGNGCCCCTTTAC GGTGGGATTCAGAGCTTACGTTG GTTTTTGGTTCCATTGCTCCCCA AACCCCGTAATCGAACCGCCGAT |

TABLE 1-continued

| SEQ ID NO: | Poly-nucleotide (DNA) or Poly-peptide (PRT) | Name | Description |
|---|---|---|---|
| | | | CGAGGTGCCGGACGGCCCTCCCC TCCCCTCTTTAGCCATTCATCTT GGCCGCACCAAAACGACGGCCGG CG |
| 6 | DNA | Ti Deletion (with N) | TAGAATGTTTCCCTCGGCTGCGA CGACCAGGCGCTCGGGATATATC CGCAGGCTGACGGGCCGGTTTGC AAATGATGCAGGCACGCTGTAGC GGTTCCGCTCGAAGGTAATCAGG CATGTTGGTGAGACGCGCTTGCT CTGCTCGACGAANGCCCCTTTAC GGTGGGATTCAGAGCTTACGTTG GTTTTTGGTTCCATTGCTCCCCA AACCCCATATGGGCGTTGTCGCG GAGATCGCTGATCGGGTTCTTGT GATGCGCGGGGCCAGGTGGTCG AGTCCGGTCCAGTGGATAGCGTG TT |
| 7 | DNA | Tn904 Deleted Sequence | Deleted Tn904 Sequence |

Plasmids useful in the methods of making the modified *Agrobacterium* strains disclosed herein are listed in Table 2 below.

TABLE 2

| SEQ ID NO: | Plasmid ID | Plasmid Components |
|---|---|---|
| 8 | V0088 | Allele-replacement vector for At chromosomal Tn904 copy |
| 9 | V0089 | Allele-replacement vector for pTi plasmid Tn904 copy |

Example 2: Generation of *A. tumefaciens* LBA4404 THY-Tn904-

The *Agrobacterium tumefaciens* strain LBA4404 and LBA4404 THY- are commonly used strains for plant transformation (Gelvin, Microbiol. Mol. Biol. Rev., (2003 March) 67(1): 16-37; Gelvin, Trends Biotechnol., (2003) 21: 95-98), (U.S. Pat. No. 8,334,429B2 (incorporated herein by reference in its entirety)). LBA4404 and LBA4404 THY- have two copies of an ~11.7 kb Tn904 transposon that were introduced during the process to create a so-called disarmed Ti plasmid that has virulence (vir) genes but lacks a T-DNA (Klapwijk et al., (1980) J. Bacteriol. 141: 129-136; Ooms, (1982) Plasmid 7(1): 15-29). One copy of Tn904 is present in the resident ~110 kb Ti plasmid and another other copy is in the ~555 kb circular chromosome of LBA4404.

The Tn904 transposon in LBA4404 and LBA4404 THY- is a composite transposon, where Tn5393 has inserted a copy of itself between tnpA and tnpR of Tn5563. The resulting composite encodes two streptomycin kinases, transposases and pin-like recombinases as well as mercuric ion transport genes merT and merP. The merT and merP proteins form an inner membrane protein complex and a periplasmic mercury ion binding protein respectively, that function to transport Hg++ into the cell. They are usually part of a larger mer operon with an intracellular mercuric reductase (Silver and Misra, (1988) Annu. Rev. Microbiol. 40:607-634), which appears to be absent in LBA4404 and LBA4404 THY-. This active transport system may affect the sensitivity of LBA4404 and LBA4404 THY- to Hg++ ions.

The two copies of the Tn904 were sequentially deleted from LBA4404 THY- (U.S. Pat. No. 8,334,429B2 (incorporated herein by reference in its entirety), using allele-replacement vectors V0088 (SEQ ID NO: 8) and V0089 (SEQ ID NO: 9), with both positive and negative selectable markers shown in FIG. 1. Tn904 can also be rendered non-functional for example by mutating one or more nucleotides, e.g., such that the composite Tn904 does not encode a functional streptomycin kinase. FIG. 1, shows a diagrammatic illustration of the generation of the Tn904- strain. A plasmid containing a Tn904-deleted allele with kb of flanking DNA of each side was cloned into a plasmid able to replicate in *E. coli*, but not *Agrobacterium*. Transformation of this plasmid into *Agrobacterium* with gentamicin selection will result in the plasmid integrating into the chromosome at a cloned region of homology. Integration can occur by recombination on either side of the plasmid allele of interest (A or B). These cells are now sensitive to sucrose, due to the sacRB allele in the plasmid. SacB encodes a levansucrase that converts sucrose to 2,6-beta-D-fructose polymers, which are toxic to a number of gram-negative bacteria including *Agrobacterium*. A second recombination event between the newly created direct repeats will lead to plasmid excision in the absence of gentamicin selection. These events can be selected by their resistance to sucrose. For excision to lead to a successful allelic exchange, recombination must occur in the second region of homology. PCR reactions using primer pairs specific to each event were then used to screen for those that deleted the Tn904 transposon.

Allele-Replacement Cassette Vectors Construction

For the deletion of both copies of the Tn904 transposon, allele-replacement cassette vectors, V0088 (SEQ ID NO: 8) and V0089 (SEQ ID NO: 9), were constructed by the overlap-based NEBuilder® HiFi (DNA assembly method available from New England Biolabs, 240 County Rd, Ipswich, MA 01938). Each vector contains 2 kb of DNA flanking the respective Tn904 insertion. All the DNA fragments containing 30 to 40 bp long overlap regions were generated by PCR or restriction enzyme digestion. PCR amplifications were done with Q5 DNA polymerase (New England Biolabs), following the manufacturer's recommendations and amplified DNA parts were analyzed by agarose gel electrophoresis and column or gel purified prior to use in the NEBuilder reaction (data not shown). Commercially available TransforMax™ EPI300™ Electrocompetent *E. coli* (Lucigen Corporation, 2905 Parmenter St, Middleton, WI 53562) were transformed with 2 µL of the assembly reaction. Assemblies were verified by sequencing.

Allele-Replacement Experiments

The two copies of Tn904 were sequentially deleted as follows. In the first-step of allele-replacement, either vector V0088 (SEQ ID NO: 8) or V0089 (SEQ ID NO: 9) were transformed into LBA4404 THY- strain by electroporation. These vectors have a ColE1 origin of replication, so they can replicate in *E. coli*, but not *Agrobacterium*. The selection for gentamicin resistant transformants results in events where the vector has integrated into the chromosome, preferentially at the cloned sites of homology flanking the Tn904 transposon. Transformants are streaked to purity on gentamicin. In the second step of allele-replacement, independent isolates are then passaged in broth without selection to allow for cells that have undergone a second recombination event, looping out the vector between the direct repeats to grow. These events no longer contain the sacRB gene and can be selected on plates containing 5% sucrose.

Colony PCR Screening for Allele-Replacement

A fraction of the sucrose-resistant candidate colonies were subjected to PCR with primers flanking the Tn904 insertion to determine if it has been deleted. Primers At.P1 (SEQ ID NO: 1): and At.P2 (SEQ ID NO: 2): were used to determine if the Tn904 allele in the At episome remained or was replaced with the synthetic deletion junction. The frequency of deletions was typically near 50%, with equal length flanking sequences suggesting no selective pressure for either allele. SEQ ID NO: 5 is the nucleotide sequence of 150 bases flanking the new Tn904 deletion region of the At episome. The "N" indicates where the Tn904 transposon (SEQ ID NO: 7) has been deleted.

The process was repeated on the LBA4404 THY-AtTn904- strain using vector V0089. Similarly, presence or absence of the Tn904 allele in the Ti plasmid was screened by colony PCR using the primers Ti.P1 (SEQ ID NO: 3): and Ti.P2 (SEQ ID NO: 4). SEQ ID NO: 6 is the nucleotide sequence of 150 bases flanking the new Tn904 deletion region of the Ti plasmid. The "N" indicates where the Tn904 transposon (SEQ ID NO: 7) has been deleted.

The new LBA4404 THY-Tn904- strain was shown to be sensitive to gentamicin, confirming loss of the integrated plasmid. This strain is now also sensitive to streptomycin, further confirming the loss of the multiple, transposon-encoded, streptomycin kinase genes.

The genome sequence of two independent isolates was determined using Illumina sequencing technology (Illumina, Inc. 5200 Illumina Way, San Diego, CA 92122) and were found to be otherwise isogenic with the previously sequenced LBA4404 THY- parent. The new LBA4404 THY-Tn904- strain was then compared with its parent for the ability to transform maize as follows.

While the methodology described above created a LBA4404 THY-Tn904- *Agrobacterium* strain, one skilled the art can use this methodology to create a Tn904-LBA4404 *Agrobacterium* strain.

Example 3: *Agrobacterium*-Mediated Transformation of Maize

A. Preparation of *Agrobacterium* Master Plate.

*Agrobacterium tumefaciens* strain LBA4404 THY- and *Agrobacterium tumefaciens* strain LBA4404 THY-Tn904- each harboring the ternary vector described below were each streaked out from a −80° C. frozen aliquot onto solid 12R medium and cultured at 28° C. in the dark for 2-3 days to make each master plate.

B. Growing *Agrobacterium* on Solid Medium.

A single colony or multiple colonies of each of *Agrobacterium tumefaciens* strain LBA4404 THY- and *Agrobacterium tumefaciens* strain LBA4404 THY-Tn904- were picked from the respective master plates and each was streaked onto a second plate containing 810K medium and incubated at 28° C. in the dark overnight.

*Agrobacterium* infection medium (700 A; 5 ml) and 100 mM 3'-5'-Dimethoxy-4'-hydroxyacetophenone (acetosyringone; 5 µL) were added to 14 mL conical tubes in a hood. About 3 full loops of each of *Agrobacterium tumefaciens* strain LBA4404 THY- and *Agrobacterium tumefaciens* strain LBA4404 THY-Tn904- from the respective second plate were suspended in one of the tubes and the tubes were then vortexed to make an even suspension. One ml of each suspension was transferred to a spectrophotometer tube and the optical density (550 nm) of each suspension was adjusted to a reading of about 0.35-1.0. The concentration of each of *Agrobacterium tumefaciens* strain LBA4404 THY- and *Agrobacterium tumefaciens* strain LBA4404 THY-Tn904- was approximately 0.5 to 2.0×10$^9$ cfu/mL. The final *Agrobacterium* suspension of each of *Agrobacterium tumefaciens* strain LBA4404 THY- and *Agrobacterium tumefaciens* strain LBA4404 THY-Tn904- was aliquoted into 2 mL microcentrifuge tubes, each containing about 1 mL of the suspension. The suspensions were then used as soon as possible.

C. Growing *Agrobacterium* on Liquid Medium.

Alternatively, *Agrobacterium tumefaciens* strain LBA4404 THY- and *Agrobacterium tumefaciens* strain LBA4404 THY-Tn904- were prepared for transformation by growing in liquid medium. One day before infection, 125 ml flasks were prepared with 30 ml of 557 A medium (10.5 g/l potassium phosphate dibasic, 4.5 g/l potassium phosphate monobasic anhydrous, 1 g/l ammonium sulfate, 0.5 g/l sodium citrate dehydrate, 10 g/l sucrose, 1 mM magnesium sulfate) and 30 µL spectinomycin (50 mg/mL) and 30 µL acetosyringone (20 mg/mL). A half loopful of each of *Agrobacterium tumefaciens* strain LBA4404 THY- and *Agrobacterium tumefaciens* strain LBA4404 THY-Tn904- each from a respective second plate was suspended into the flasks and placed on an orbital shaker set at 200 rpm and incubated at 28° C. overnight. The *Agrobacterium tumefaciens* strain LBA4404 THY- and *Agrobacterium tumefaciens* strain LBA4404 THY-Tn904- cultures were each centrifuged at 5000 rpm for 10 min. The supernatants were removed and the *Agrobacterium* infection medium (700 A) with acetosyringone solution was added. The bacteria were resuspended by vortex and the optical density (550 nm) of each *Agrobacterium* suspension was adjusted to a reading of about 0.35 to 2.0.

D. Maize Transformation.

Ears of maize (*Zea mays* L.) cultivars, HC69 or PH2RT, were surface-sterilized for 15-20 min in 20% (v/v) bleach (5.25% sodium hypochlorite) plus 1 drop of Tween 20 followed by 3 washes in sterile water. Immature embryos (IEs) were isolated from ears and were placed in 2 ml of the *Agrobacterium* infection medium (700 A) with acetosyringone solution containing either *Agrobacterium tumefaciens* strain LBA4404 THY- or *Agrobacterium tumefaciens* strain LBA4404 THY-Tn904-. The optimal size of the embryos was 1.5-1.8 mm for HC69 and PH2RT, respectively. The solution was drawn off and 1 ml of the *Agrobacterium* suspension containing either *Agrobacterium tumefaciens* strain LBA4404 THY- or *Agrobacterium tumefaciens* strain LBA4404 THY-Tn904- was added to each of the HC69 and PH2RT embryos and the tubes were vortexed for 5-10 sec. The microfuge tubes were allowed to stand for 5 min in the hood. The suspensions of *Agrobacterium* and embryos were poured onto 710I (or 562V) co-cultivation medium (see Table 9). Any embryos left in the tube were transferred to the respective plates using a sterile spatula. The *Agrobacterium* suspension was drawn off and the embryos were placed axis side down on the media. The plates were incubated in the dark at 21° C. for 1-3 days of co-cultivation.

Embryos were then transferred to resting medium (605T medium) without selection. Three to 7 days later, the embryos were transferred to maturation medium (289Q medium) supplemented with a selective agent (see Table 9).

Example 4: LBA4404 THY-Tn904- Maize Transformation

The transposon minus strain, LBA4404 THY-Tn904-, was tested for maize transformation in inbreds HC69 and PH2RT, using the co-habitating vector system containing the pVIR plasmid, pPHP71539 (pVIR9), disclosed in US Patent Publication 2019/0078106, incorporated herein in its entirety). Transformation experiments were conducted to compare the stable transformation efficiency between LBA4404 THY–Tn904– (TN) and its parent strain LBA4404 THY– (Control) using two constructs (Construct A and Construct B). Transformations were performed as described in Example 4. Transformation rates were evaluated in terms of callus transformation frequency (L2%), regenerated event frequency (L3), Reg % is the regeneration percentage (how many of the L2 Events that regenerated in to plants), T0 event number and frequency (L4 & T0 %), quality event frequency (the percentage of events with all transgenes of interest being single copy and free of vector backbone DNA) and usable quality event (defined as the number of QE (Quality Event) events recovered for every 100 embryos infected UE (Usable Event) %) (Useable Event is the ratio of OE/# of infected embryos) for the two vectors (Construct A and Construct B) in the two different *Agrobacterium* strains LBA4404 THY–Tn904– and LBA4404 THY–. The transformation experiments were conducted with a minimum of 500 embryos and the transformation results are presented in the Table 3 and Table 4.

TABLE 3

| Construct | Inbred Genotype | Treatment | # Adj Emb | # L2 Event | L2 % | Reg % | # L3 |
|---|---|---|---|---|---|---|---|
| A | HC69 | Control | 523 | 320 | 61% | 46% | 148 |
| A | HC69 | Tn904– | 510 | 288 | 56% | 57% | 164 |
| B | PH2RT | Control | 510 | 411 | 81% | 51% | 203 |
| B | PH2RT | Tn904– | 510 | 385 | 75% | 49% | 188 |

TABLE 4

| Construct | Inbred Genotype | Treatment | # L4 T0s | # QE | T0 % | QE % | UQE % |
|---|---|---|---|---|---|---|---|
| A | HC69 | Control | 88 | 27 | 28% | 31% | 8.9% |
| A | HC69 | Tn904– | 100 | 27 | 32% | 28% | 9.0% |
| B | PH2RT | Control | 150 | 23 | 40% | 15% | 6.1% |
| B | PH2RT | Tn904– | 148 | 34 | 37% | 23% | 8.5% |

As shown in Table 3 and Table 4 no statistically significant differences were observed in transformation frequency and event quality between the two strains LBA4404 THY–Tn904– (TN) and its parent strain LBA4404 THY– (Control).

Example 5: Transformation of Other Plant Species

It is expected that the Tn904– *Agrobacterium* strains disclosed herein will perform comparably to the parent strain when transforming other plant species. Specifically, it is expected that Tn904– *Agrobacterium* strains disclosed herein will provide transformation and quality event frequencies similar to the parent strain.

Example 6: Sorghum Transformation

Freshly harvested immature grains of sorghum variety Tx430 with embryo sizes between 2.2-2.5 mm were sterilized with 50% bleach and 0.1% Tween-20 for thirty (30) minutes under vacuum and then rinsed with sterile water three (3) times. *Agrobacterium* strain LBA4404 THY–Tn904– containing Construct C was adjusted to an OD of 1.0 (550 nm) in liquid 700 A medium, and immature sorghum embryos were added to the *Agrobacterium* suspension for 5 minutes at room temperature (25° C.). After the 5-minute liquid infection treatment, the immature embryos were removed from the liquid medium and transferred onto solid medium 710I and oriented scutellum-side up for culture at 21° C. in the dark overnight.

The embryos were subjected to the following sequential steps after infection: (1) co-cultivation: embryos were cultured on 710I medium following infection for six (6) days at 25° C. in the dark; (2) resting: embryos were cultured on 13152C medium for seven (7) days at 28° C. in the dark; (3) selection: embryos were cultured on 13329F medium for four (4) weeks in the dark to stimulate shoot development; (4) the regenerated shoots were subcultured on 13113 A medium (13113 A contains half-strength MS salts and vitamins, 0.05 g/l myo-inositol, 20 g/l sucrose, and 3 g/l phytagel, pH5.6) for two (2) to three (3) weeks under lights (40-120 µE m-2 s-1) to stimulate root growth; and (5) the regenerated plantlets were then transplanted into soil and grown in the greenhouse.

The results are shown in Table 5. Transformation efficiency was calculated as the number of regenerated shoots recovered per one-hundred (100) embryos infected. The integrated copy number of the T-DNA and the vector backbone in these transgenic plants were determined by a series of qPCR analyses. Transgenic plants having a single copy of the intact T-DNA integration without vector backbone were defined as 'Quality Events'.

TABLE 5

| Construct | Variety | # of Embryos Infected | # of Events Recovered | Transformation Efficiency (%) | Quality Events (%) |
|---|---|---|---|---|---|
| C | Tx430 | 241 | 131 | 54.4% | 51.1% |

The results in Table 5 show that *Agrobacterium* strain LBA4404 THY–Tn904– provides transformation efficiencies in sorghum comparable to its parent *Agrobacterium* strain LBA4404 THY– (data not shown).

Example 7: Canola Transformation

Seeds of *Brassica napus* 4PYZE50B were surface sterilized in a 50% Clorox solution and germinated on solid medium containing MS basal salts and vitamins. The seedlings were grown at 28° C. in the light for ten to fourteen days, and internodal segments were dissected from the seedlings. The internodal segment explants were transferred into 100×25 mm petri plates containing 10 mls of 20 A medium and then sliced into sections 3-5 mm long. After slicing, 40 µl of *Agrobacterium* strain LBA4404 THY–Tn904– solution (at an Optical Density of 0.50 at 550 nm) with each strain containing one (1) of eighteen (18) constructs (Construct D-Construct U) was added to the plates, and the petri plates containing the internodal segments/*Agrobacterium* LBA4404 THY–Tn904– mixture were placed on a shaker platform and lightly agitated for ten minutes. After ten minutes of gentle agitation, the plates were moved into dim light and 21° C. for three days of co-cultivation.

After co-cultivation, the internodal segment explants were removed from the *Agrobacterium* LBA4404 THY–Tn904– solution, and lightly blotted onto sterile filter paper before placing onto 70 A selection media and moved to the light room (26° C. and bright light). Explants remained on 70 A selection media for two weeks prior to transfer to a second round of 70 A selection. After two rounds of selection the explants were transferred to 70 C shoot elongation media for two to three weeks and placed back into the light room. Shoots were then transferred onto 90 A rooting media (MS salts and vitamins; 0.5 mg/l IBA; pH 5.7) before being transferred to soil in the greenhouse. Rooted plants were tabulated.

Gene editing target sites were analyzed via two-step PCR amplification and Illumina sequencing to confirm edits. The results are shown in Table 6.

TABLE 6

| Construct | # Of Internodal Segments Infected | # Of Rooted Plants Recovered | Transformation Efficiency (%) |
| --- | --- | --- | --- |
| D | 1574 | 87 | 5.5% |
| E | 1500 | 76 | 5.1% |
| F | 1543 | 52 | 3.4% |
| G | 1083 | 59 | 5.4% |
| H | 1252 | 40 | 3.2% |
| I | 1454 | 33 | 2.3% |
| J | 1229 | 45 | 3.7% |
| K | 1060 | 45 | 4.2% |
| L | 1000 | 61 | 6.1% |
| M | 1000 | 40 | 4.0% |
| N | 1000 | 57 | 5.7% |
| O | 1000 | 15 | 1.5% |
| P | 1000 | 57 | 5.7% |
| Q | 1000 | 113 | 11.3% |
| R | 1000 | 32 | 3.2% |
| S | 1000 | 36 | 3.6% |
| T | 1000 | 21 | 2.1% |
| U | 1000 | 53 | 5.3% |

The results in Table 6 show that *Agrobacterium* strain LBA4404 THY−Tn904− provides transformation efficiencies in canola comparable to its parent *Agrobacterium* strain LBA4404 THY− (data not shown).

Example 8: Sunflower Transformation

*Agrobacterium* strain LBA4404 THY− Tn904− was used for sunflower (*Helianthus annuus* Variety A and Variety B) transformation. Mature dry sunflower seeds were sterilized in a bleach solution (10-15% v/v in water with one drop of Tween detergent) for fifteen (15) minutes and then rinsed three (3) times in sterile water. Seeds were imbibed overnight. The embryos were removed from the softened hulls. Once the embryos were isolated, incisions were made at the base of the cotyledons to facilitate embryo isolation thereby exposing the leaf primordia sheathing the apical meristem. The radical tip was left attached to the embryo. After isolation, embryo axes (EAs) were transferred to petri plates for infection.

The *Agrobacterium* LBA4404 THY− Tn904− strain containing a plasmid with a T-DNA containing expression cassette Construct V was used for transformation. The *Agrobacterium* LBA4404 THY− Tn904− strain was suspended in 20 A media and the concentration of the bacterial suspensions were adjusted to 0.5 OD550. The EAs were then placed under vacuum with gentle agitation for twenty (20) minutes. The EAs were removed from the *Agrobacterium* LBA4404 THY− Tn904− and inserted radicle-end down into 272AC medium (standard MS salts and vitamin levels (Murashige and Skoog, 1962, Physiol. Plant 15:473-497), 0.1 g/l myo-inositol, 50 mg/l thymidine, 100 µM acetosyringone, 0.1 mg/l BAP, 40 g/l sucrose, 6 g/l Bacto Agar, pH 5.6), leaving the apical dome above the 272AC medium, and placed under dim light at 21° C. for three days of co-cultivation. After co-cultivation, the EAs were transferred to 272AB spectinomycin selection media (standard MS salts and vitamin levels (Murashige and Skoog, 1962, Physiol. Plant 15:473-497), 0.1 g/l myo-inositol, 10 mg/l meropenem, 0.1 mg/l meta-Topolin (mT), 30 mg/l spectinomycin dihydrochloride, 0.1 ug/l, 40 g/l sucrose, 6 g/l Bacto Agar, pH 5.6) under full light at 28° C.

The EAs were allowed to grow, with periodic trimming of bleached leaves. Within approximately three weeks after exposure to spectinomycin, green sectors or whole green leaves were observed. This green tissue also expressed DS-RED, confirming that the T-DNA from Construct V had been integrated. For rooting, transgenic events were transferred to a Bio-Dome Sponge rooting material (Park Seed Co., 3507 Cokesbury Road, Hodges, SC). After transfer to the Bio-Dome Sponge rooting material, roots formed within one to three weeks and the plants were potted and transferred to the greenhouse or growth-chambers. Regenerated plants were tabulated.

All plants produced in this experiment were sampled for qPCR analysis to confirm integration of Construct V. The results are shown in Table 7.

TABLE 7

| Construct V | Variety A | Variety B |
| --- | --- | --- |
| Number of explants infected | 849 | 849 |
| Transformed T0 events recovered | 29 | 20 |
| Transformation efficiency (%) | 3.4 | 2.4 |

The results in Table 7 show that *Agrobacterium* strain LBA4404 THY−Tn904− provides transformation efficiencies in sunflower comparable to its parent *Agrobacterium* strain LBA4404 THY− (data not shown).

Example 9: Wheat Transformation

Freshly harvested wheat immature grains of Spring wheat variety SBC0456D were sterilized with 50% bleach and 0.1% Tween-20 for thirty (30) minutes under vacuum and then rinsed with sterile water three times. *Agrobacterium* strain LBA4404 THY− Tn904− solution (at an Optical Density of OD of 1.0 (600 nm)) in liquid 716B medium, with each strain containing one (1) of fourteen (14) constructs (Construct AA-Construct NN) and immature wheat embryos were added to the *Agrobacterium* LBA4404 THY− Tn904− suspension for twenty (20) minutes at room temperature (25° C.). After a 15-minute liquid infection treatment, the immature embryos were removed from the liquid medium and transferred onto solid 606 medium and oriented scutellum-side up for culture at 21° C. in the dark overnight. The embryos were transferred again onto fresh resting medium (606) for ten (10) days, then onto regeneration medium 689E with selection in the dark. The tissue was then moved onto regeneration medium 689E with selection in the light and then the number of plants produced was tabulated.

The integrated copy number of the T-DNA and the vector backbone in these transgenic plants were determined by a series of qPCR analyses. Transgenic plants having a single copy of the intact T-DNA integration without vector backbone were defined as 'Quality Events'. The results are shown in Table 8.

TABLE 8

| Construct | # Of Embryos Infected | T0s Sent To Greenhouse | Transformation Efficiency (%) | Quality Events (%) |
|---|---|---|---|---|
| AA | 200 | 120 | 60.0% | 6.7% |
| BB | 200 | 120 | 60.0% | 5.8% |
| CC | 200 | 120 | 60.0% | 10.8% |
| DD | 200 | 151 | 75.5% | 6.6% |
| EE | 200 | 120 | 60.0% | 10.0% |
| FF | 200 | 120 | 60.0% | 7.5% |
| GG | 200 | 120 | 60.0% | 12.5% |
| HH | 200 | 120 | 60.0% | 5.0% |
| II | 200 | 120 | 60.0% | 8.3% |
| JJ | 200 | 120 | 60.0% | 10.0% |
| KK | 200 | 120 | 60.0% | 9.2% |
| LL | 200 | 197 | 98.5% | 3.0% |
| MM | 200 | 192 | 96.0% | 4.7% |
| NN | 200 | 130 | 65.0% | 4.6% |

The results in Table 8 show that *Agrobacterium* strain LBA4404 THY−Tn904− (TN) provides transformation efficiencies in sorghum comparable to its parent *Agrobacterium* strain LBA4404 THY− (data not shown).

Example 10: Culture Media

See Tables 9-14 for a description of the media formations for transformation, resting, selection and regeneration referenced in the Examples.

TABLE 9

| Medium components | Units per liter | 12R | 810K | 700A | 710I | 605J | 605T | 562V | 289Q |
|---|---|---|---|---|---|---|---|---|---|
| MS BASAL SALT MIXTURE | g | | | 4.3 | 4.3 | 4.3 | 4.3 | | 4.3 |
| N6 BASAL SALTS | g | | | | | | | 4.0 | |
| N6 MACRONUTRIENTS 10X | ml | | | | | 60.0 | 60.0 | | |
| POTASSIUM NITRATE | g | | | | | 1.7 | 1.7 | | |
| B5H MINOR SALTS 1000X | ml | | | | | 0.6 | 0.6 | | |
| NaFe EDTA FOR B5H 100X | ml | | | | | 6.0 | 6.0 | | |
| ERIKSSON'S VITAMINS 1000X | ml | | | | | 0.4 | 0.4 | 1.0 | |
| S&H VITAMIN STOCK 100X | ml | | | | | 6.0 | 6.0 | | |
| THIAMINE•HCL | mg | | | 10.0 | 10.0 | 0.5 | 0.5 | 0.5 | |
| L-PROLINE | g | | | | 0.7 | 2.0 | 2.0 | 0.69 | 0.7 |
| CASEIN HYDROLYSATE (ACID) | g | | | | | 0.3 | 0.3 | | |
| SUCROSE | g | | | 68.5 | 20.0 | 20.0 | 20.0 | 30.0 | 60.0 |
| GLUCOSE | g | 5.0 | | 36.0 | 10.0 | 0.6 | 0.6 | | |
| MALTOSE | g | | | | | | | | |
| 2,4-D | mg | | | 1.5 | 2.0 | 0.8 | 0.8 | 2.0 | |
| AGAR | g | 15.0 | | | 8.0 | 6.0 | 6.0 | 8.0 | 8.0 |
| BACTO-AGAR | g | | 15.0 | | | | | | |
| PHYTAGEL | g | | | | | | | | |
| DICAMBA | g | | | | | 1.2 | 1.2 | | |
| SILVER NITRATE | mg | | | | | 3.4 | 3.4 | 0.85 | |
| AGRIBIO Carbenicillin | mg | | | | 100.0 | | | | |
| Timentin | mg | | | | | 150.0 | | 150.0 | |
| Cefotaxime | mg | | | | | 100.0 | | 100.0 | |
| MYO-INOSITOL | g | | | 0.1 | 0.1 | | | | 0.1 |
| NICOTINIC ACID | mg | | | 0.5 | 0.5 | | | | |
| PYRIDOXINE•HCL | mg | | | 0.5 | 0.5 | | | | |
| VITAMIN ASSAY CASAMINO ACIDS | g | | | 1.0 | | | | | |
| MES BUFFER | g | | | | 0.5 | | | | |
| ACETOSYRINGONE | μM | | | | 100.0 | | | 100.0 | |
| ASCORBIC ACID 10 MG/ML (7S) | mg | | | | 10.0 | | | | |
| MS VITAMIN STOCK SOL. | ml | | | | | | | | 5.0 |
| ZEATIN | mg | | | | | | | | 0.5 |
| CUPRIC SULFATE | mg | | | | | | | | 1.3 |
| IAA 0.5 MG/ML (28A) | ml | | | | | | | | 2.0 |
| ABA 0.1 mm | ml | | | | | | | | 1.0 |
| THIDIAZURON | mg | | | | | | | | 0.1 |
| AGRIBIO Carbenicillin | mg | | | | | | | | 100.0 |

TABLE 9-continued

| Medium components | Units per liter | 12R | 810K | 700A | 710I | 605J | 605T | 562V | 289Q |
|---|---|---|---|---|---|---|---|---|---|
| PPT(GLUFOSINATE-NH4) | mg | | | | | | | | |
| BAP | mg | | | | | | | | 1.0 |
| YEAST EXTRACT (BD Difco) | g | | 5.0 | | | | | | |
| PEPTONE | g | | 10.0 | | | | | | |
| SODIUM CHLORIDE | g | | 5.0 | | | | | | |
| SPECTINOMYCIN | mg | 50.0 | 50.0 | | | | | | |
| FERROUS SULFATE•7H2O | ml | 2.0 | | | | | | | |
| AB BUFFER 20X (12D) | ml | 50.0 | | | | | | | |
| AB SALTS 20X (12E) | ml | 50.0 | | | | | | | |
| THYMIDINE | mg | 50.0 | 50.0 | 50.0 | | | | 50.0 | |
| GENTAMYCIN | mg | 50.0 | 50.0 | | | | | | |
| Benomyl | mg | | | | | | | | |
| pH | | | 6.8 | 5.2 | 5.8 | 5.8 | 5.8 | 5.8 | 5.6 |

TABLE 10

| Medium components | Units per liter | 20A | 70A | 70B | 70C |
|---|---|---|---|---|---|
| MS BASAL SALT MIXTURE | g | 4.3 | 4.3 | 4.3 | 4.3 |
| THIAMINE•HCL | mg | 0.12 | 0.12 | 0.12 | 0.12 |
| SUCROSE | g | | 20 | 20 | 20 |
| PVP40 | g | | 0.5 | 0.5 | 0.5 |
| TC AGAR | g | | 5 | 5 | 5 |
| SILVER NITRATE | mg | | 2.0 | 2.0 | 2.0 |
| AGRIBIO Carbenicillin | g | | 0.5 | 0.5 | 0.5 |
| Adenine Hemisulfate Salt | mg | | 40 | 40 | 40 |
| MYO-INOSITOL | g | 0.1 | 0.1 | 0.1 | 0.1 |
| NICOTINIC ACID | mg | 0.57 | 0.57 | 0.57 | 0.57 |
| PYRIDOXINE•HCL | mg | 0.57 | 0.57 | 0.57 | 0.57 |
| Glycine | mg | 2.3 | 2.3 | 2.3 | 2.3 |
| MES BUFFER | g | 0.5 | 0.5 | 0.5 | 0.5 |
| ACETOSYRINGONE | μM | 200 | | | |
| NAA | mg | 0.1 | 0.1 | 0.1 | 0.1 |
| BAP | mg | 1.0 | 1.0 | 1.0 | 1.0 |
| Gibberellic Acid | ug | 10 | 10 | 10 | 10 |
| SPECTINOMYCIN | mg | | 5 | 10 | 10 |
| pH | | | 5.7 | 5.7 | 5.7 |

The compositions of various media used in soybean transformation, tissue culture and regeneration are outlined in Table 11. In this table, medium M1 is used for initiation of suspension cultures, if this is the starting material for transformation. Media M2 and M3 represent typical co-cultivation media useful for *Agrobacterium* transformation of the entire range of explants listed above. Medium M4 is useful for selection (with the appropriate selective agent), M5 is used for somatic embryo maturation, and medium M6 is used for germination to produce TO plantlets.

TABLE 11

| | M1 | M2 | M3 | M4 | M5 | M6 |
|---|---|---|---|---|---|---|
| MS salt with B5 vitamins (PhytoTech M404) | 4.44 g/L | | | 4.4 g/L | 4.44 g/L | |
| Gamborg B-5 basal medium (PhytoTech G398) | | | | | | 3.21 g/L |
| Modified MS salt (PhytoTech M571) | | 2.68 g/L | 2.68 g/L | | | |
| B5 vitamins (1000X) (PhytoTech G249) | | 1 ml | 1 ml | 1 ml | | |
| 2,4-D stock 10 mg/ml | 4 ml | 1 ml | 1 ml | 4 ml | | |
| KNO3 | | 1.64 g/L | 1.64 g/L | | | |
| (NH4)2SO4 | | 0.463 g/L | 0.463 g/L | | | |
| Asparagine | | 1 g/L | 1 g/L | | | |
| Sucrose | | 68.5 g/L | 85.6 g/L | | | 20 g/L |
| Glucose | 31.5 g/L | 36 g/L | 49.6 g/L | 31.5 g/l | | |
| Maltose | | | | | 60 g/L | |
| MgCl2•6H2O | | | | | 0.75 g/L | |
| Activated charcoal (PhytoTech C325) | | | | | 5 g/L | |
| Casein hydrolysate (PhytoTech C184) | | 1 g/L | 1 g/L | | | |

TABLE 11-continued

|  | M1 | M2 | M3 | M4 | M5 | M6 |
| --- | --- | --- | --- | --- | --- | --- |
| pH | 7.0 | 5.4 | 5.4 | 7.0 | 5.7 | 5.7 |
| Acetosyringone |  | 300 μM | 300 μM |  |  |  |
| TC agar | 4 g/L |  |  |  |  | 5 g/L |
| Gelrite (Plant Media Cat# 714246) |  |  |  | 2 g/l | 2 g/L |  |

TABLE 12

| Medium Components | Units per liter | 13152C |
| --- | --- | --- |
| MS BASAL SALT MIXTURE | g | 4.3 |
| THIAMINE •HCL | mg | 1.0 |
| L-PROLINE | G | 0.7 |
| CASEIN HYDROLYSATE (ACID) | g | 1.0 |
| MALTOSE | g | 30.0 |
| 2,4-D | mg | 1.0 |
| PHYTAGEL | g | 3.5 |
| MYO-INOSITOL | g | 0.25 |
| CUPRIC SULFATE (100 mM) | ml | 1.22 |
| AGRIBIO Carbenicillin | mg | 100 |
| BAP (1 mg/ml) | mg | 0.5 |
| pH |  | 5.8 |

TABLE 13

| 13329F Medium Components | Concentration |
| --- | --- |
| MS salt | 4.3 g/l |
| Myo-Inositol | 0.1 g/l |
| MS vitamins stock (0.1 g/l nicotinic acid, 0.1 g/l pyridoxine HCl, 0.02 g/l thiamine HCl, 0.4 g/l glycine) | 5 ml/l |
| zeatin | 0.5 mg/l |
| Cupric sulfate | 1.25 mg/l |
| L-Proline | 0.7 g/l |
| Sucrose | 60 g/l |
| Phytagel | 3.5 g/l |
| Indole-3-acetic acid | 1 mg/l |
| ABA | 0.1 μM |
| Thidiazuron | 0.1 mg/l |
| Carbenicillin | 100 mg/l |
| G410 | 250 mg/l |

TABLE 14

Media used for wheat transformation.

| Ingredient | 716B Quantity | 606 Quantity | 689E Quantity |
| --- | --- | --- | --- |
| D-I WATER, POLISHED | 950 ml | 950 ml | 950 ml |
| MS BASAL SALT MIXTURE | 4.3 g | 4.3 g | 4.3 g |
| CHU(N6) BASAL SALTS |  | 2.39 g |  |
| POTASSIUM NITRATE |  | 1.68 g |  |
| B5H MINOR SALTS 1000X |  | 0.6 ml |  |
| NaFe EDTA FOR B5H 100X |  | 6 ml |  |
| ERIKSSON'S VITAMINS 1000X |  | 0.4 ml |  |
| S&H VITAMIN STOCK 100X |  | 6 ml |  |
| L-PROLINE |  | 1.98 g |  |
| CASEIN HYDROLYSATE (ACID) |  | 0.3 g |  |
| MALTOSE |  | 30 g |  |
| GLUCOSE |  | 10 g |  |
| MYO-INOSITOL | 0.1 g |  | 1.1 g |
| MS VITAMIN STOCK SOLN* | 5 ml |  | 5 ml |
| 2,4-D 0.5 mg/ml | 1 ml | 1.6 ml |  |
| CUPRIC SULFATE 1 MG/ML |  | 1.22 ml |  |
| BAP 1 MG/ML |  | 0.5 ml |  |
| Picloram 10 mg/ml | 0.2 ml |  |  |
| MALTOSE | 30 g |  |  |
| MES BUFFER | 1.95 g |  |  |
| CUPRIC SULFATE 1 MG/ML | 1.22 ml |  |  |
| BAP 1 MG/ML | 0.5 ml |  |  |
| TC-AGAR |  |  | 6 g |
| PHYTAGEL | 2.5 g | 3.5 g | 3.5 g |
| pH | 5.8 | 5.8 | 5.8 |
| ACETOSYRINGONE 100 mM | 4 ml |  |  |
| thymidine (50 mg/ml) | 1 ml | 0.5 ml |  |
| Dicamba (1 mg/ml) |  | 1.2 ml |  |
| Cefotaxime (250 mg/ml) |  | 0.4 ml | 0.4 ml |
| sucrose |  |  | 60 g |
| phosphinothricin (1 mg/ml) |  |  | 5 ml |

*MS Vitamin Stock: 0.1 g/l nicotinic acid, 0.02 g/l thiamine, 0.1 g/l pyridoxine, 0.4 g/l glycine As used herein the singular forms "a", "an", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

All patents, publications and patent applications mentioned in the specification are indicative of the level of those skilled in the art to which this disclosure pertains. All patents, publications and patent applications are herein incorporated by reference in the entirety to the same extent as if each individual patent, publication or patent application was specifically and individually indicated to be incorporated by reference in its entirety.

Although the foregoing disclosure has been described in some detail by way of illustration and example for purposes of clarity of understanding, certain changes and modifications may be practiced within the scope of the appended claims.

That which is claimed:

1. A genetically modified *Agrobacterium tumefaciens* bacterium comprising SEQ ID NO:5 and SEQ ID NO:6 and a deficient Tn904 transposon, wherein a functional Tn904 transposon is not present.

2. The modified *Agrobacterium tumefaciens* bacterium of claim 1, wherein the *Agrobacterium tumefaciens* bacterium demonstrates sensitivity to streptomycin due to the non-functional Tn904 transposon.

3. The modified *Agrobacterium tumefaciens* bacterium of claim 1, wherein the Tn904 transposon is rendered non-functional by allele replacement.

4. The modified *Agrobacterium tumefaciens* bacterium of claim 1, wherein the Tn904 transposon comprises a sequence that is at least 95% identical to SEQ ID NO: 7.

5. The modified *Agrobacterium tumefaciens* bacterium of claim 1, further comprising a binary plasmid comprising a T-DNA having a polynucleotide of interest encoding a polypeptide that confers a trait to a plant.

6. The modified *Agrobacterium tumefaciens* bacterium of claim 5, wherein the trait conferred is selected from the group consisting of a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing.

7. The modified *Agrobacterium tumefaciens* bacterium of claim 1, further comprising a disarmed Ti plasmid.

8. The modified *Agrobacterium tumefaciens* bacterium of claim 7, further comprising a binary plasmid comprising a T-DNA with a polynucleotide of interest encoding a polypeptide that confers a trait to a plant.

9. The modified *Agrobacterium tumefaciens* bacterium of claim 8, wherein the trait conferred is selected from the group consisting of a nutritional enhancement, a modified oil content, a modified protein content, a modified metabolite content, increased yield, abiotic stress tolerance, drought tolerance, cold tolerance, herbicide tolerance, pest resistance, pathogen resistance, insect resistance, nitrogen use efficiency (NUE), disease resistance, increased biomass, an ability to alter a metabolic pathway, and a combination of the foregoing.

10. The modified *Agrobacterium tumefaciens* bacterium of claim 7, wherein the disarmed Ti plasmid is pVIR9.

11. The modified *Agrobacterium tumefaciens* bacterium of claim 5, further comprising a pVIR9 plasmid.

12. The modified *Agrobacterium tumefaciens* strain of claim 1, wherein its parent strain is *Agrobacterium tumefaciens* LBA4404.

13. The modified *Agrobacterium tumefaciens* strain of claim 1, wherein its parent strain is *Agrobacterium tumefaciens* LBA4404 THY$^-$.

* * * * *